(12) United States Patent
Becker et al.

(10) Patent No.: US 7,091,200 B2
(45) Date of Patent: Aug. 15, 2006

(54) QUINAZOLONE DERIVATIVES AS ALPHA 1A/B ADRENERGIC RECEPTOR ANTAGONISTS

(75) Inventors: Cyrus Kephra Becker, Menlo Park, CA (US); Joan Marie Caroon, Mountain View, CA (US); Chris Richard Melville, Palo Alto, CA (US); Fernando Padilla, Fremont, CA (US); Jürg Roland Pfister, Los Altos, CA (US); Xiaoming Zhang, Campbell, CA (US)

(73) Assignee: Syntex U.S.A. LLC, Palo Alto, CA (US)

( * ) Notice: Subject to any disclaimer, the term of this patent is extended or adjusted under 35 U.S.C. 154(b) by 0 days.

(21) Appl. No.: 10/971,522

(22) Filed: Oct. 22, 2004

(65) Prior Publication Data

US 2005/0107365 A1 May 19, 2005

Related U.S. Application Data

(62) Division of application No. 10/040,319, filed on Jan. 2, 2002, now Pat. No. 6,900,220.

(60) Provisional application No. 60/325,267, filed on Sep. 27, 2001, provisional application No. 60/259,337, filed on Jan. 2, 2001.

(51) Int. Cl.
  *A61K 31/54* (2006.01)
  *A61P 13/08* (2006.01)
  *C07D 285/22* (2006.01)
  *A61K 31/549* (2006.01)
  *A61K 31/517* (2006.01)
  *A61K 31/519* (2006.01)
  *C07D 487/04* (2006.01)
  *C07D 241/36* (2006.01)
  *C07D 471/02* (2006.01)

(52) U.S. Cl. ............. 514/223.2; 514/259.1; 514/266.21; 544/12; 544/13; 544/281; 544/284

(58) Field of Classification Search ............ 514/223.2, 514/259.1, 266.21; 544/12, 13, 281, 284
See application file for complete search history.

(56) References Cited

U.S. PATENT DOCUMENTS

| | | | | |
|---|---|---|---|---|
| 3,146,233 A | * | 8/1964 | Hurmer | 544/13 |
| 3,275,625 A | * | 9/1966 | Muller et al. | 544/13 |
| 3,892,858 A | * | 7/1975 | Novello | 514/223.2 |
| 3,960,861 A | | 6/1976 | Danilewicz et al. | 260/256.4 |
| 4,029,780 A | * | 6/1977 | Nishimura et al. | 514/223.2 |
| 4,044,136 A | | 8/1977 | Danilewicz et al. | 424/251 |
| 4,171,361 A | * | 10/1979 | Dillard et al. | 514/218 |
| 4,686,228 A | | 8/1987 | Campbell et al. | 514/307 |
| 4,766,211 A | * | 8/1988 | Zink et al. | 544/58.6 |
| 5,064,833 A | * | 11/1991 | Ife et al. | 514/266.4 |
| 5,488,049 A | * | 1/1996 | Costa et al. | 514/223.2 |
| 5,773,434 A | * | 6/1998 | Larson et al. | 514/212.03 |
| 6,030,968 A | * | 2/2000 | Gall et al. | 514/223.2 |
| 6,103,738 A | | 8/2000 | Collis et al. | 514/311 |
| 6,337,332 B1 | * | 1/2002 | Carpino | 514/252.17 |
| 6,492,358 B1 | * | 12/2002 | Sui et al. | 514/232.8 |
| 6,562,854 B1 | * | 5/2003 | Church et al. | 514/394 |
| 6,566,367 B1 | * | 5/2003 | Bakthavatchalam et al. | 514/278 |

(Continued)

FOREIGN PATENT DOCUMENTS

| | | |
|---|---|---|
| DE | 2757925 A1 | 6/1979 |
| GB | 1062357 | 3/1967 |
| WO | WO 98/30560 A1 | 7/1998 |
| WO | WO 00/55143 A1 | 9/2000 |

OTHER PUBLICATIONS

Gupta, et al., "Drugs Acting on the Central Nervous System. Syntheses of Substituted Quinazolones and Quanazolines and Triazepino- and Triazocinoquina-zolones," *J. Med. Chem.*, 1968, 392-395, 11(2).

(Continued)

*Primary Examiner*—James O. Wilson
*Assistant Examiner*—Tamthom N. Truong
(74) *Attorney, Agent, or Firm*—Grant D. Green

(57) ABSTRACT

This invention relates to compounds which are generally alpha-1A/B adrenoceptor antagonists and which are represented by Formula I:

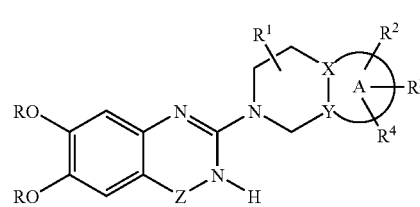

wherein Z is —C(O)— or —S(O)$_2$—, X is carbon or nitrogen, Y is carbon, and X-Y considered together are two adjoining atoms of the ring A, said ring being a fused aromatic ring of five to six atoms per ring optionally incorporating one to two heteroatoms per ring, chosen from N, O, or S; and the other substituents are as defined in the specification; or individual isomers, racemic or non-racemic mixtures of isomers, or pharmaceutically acceptable salts or solvates thereof. The invention further relates to pharmaceutical compositions containing such compounds, methods for their use as therapeutic agents, and methods of preparation thereof.

24 Claims, No Drawings

U.S. PATENT DOCUMENTS

2002/0119969 A1* 8/2002 Ebdrup et al. ............ 514/222.8
2003/0109519 A1* 6/2003 Sturis ........................ 514/223.2
2004/0029859 A1* 2/2004 Blagg et al. ............ 514/210.21

OTHER PUBLICATIONS

Leonardi, et al., "Synthesis Pharmacological Evaluation, and Structure—Activity Relationship and Quantitative Structure—Activity Relationship Studies on Novel Derivatives of 2,4-Diamino-6,7-dimethoxyquinazoline $\alpha_1$-Adrenoceptor Antagonists", *J. Med. Chem.*, 1999, 427-437, 42.

Menziani, et al., "Relevance of Theoretical Molecular Descriptors in Quantitative Structure—Activity Relationship Analysis of $\alpha$1-Adrenergic Receptor Antagonists," *Bioorg., Med. Chem.*, 1999, 2437-2451, 7(11).

Villalorgo, et al., "Solid-Phase Synthesis of 3H-Quinazolin-4-ones Based on an Aza Wittig-Mediated annulation Strategy", *Synlett*, 1998, 1405-1407, 12.

Wollweber, et al., "3-Amino-2H-1,2,4-benzothiadiazin-1, 1-dioxide mit antihypertensiver und potentieller diabetogener Wirkung", *Arzneim.-Forsch.*, 1981, 279-88, 31(2).

* cited by examiner

QUINAZOLONE DERIVATIVES AS ALPHA 1A/B ADRENERGIC RECEPTOR ANTAGONISTS

CROSS REFERENCE TO RELATED INVENTIONS

This Application is a division of and claims priority from U.S. Ser. No. 10/040,319, filed Jan. 2, 2002 now U.S. Pat. No. 6,900,220, and claims priority from U.S. Ser. No. 60/259,337, filed Jan. 2, 2001 and U.S. Ser. No. 60/325,267, filed Sep. 27, 2001; each of which is hereby incorporated by reference in its entirety.

FIELD OF THE INVENTION

This invention relates to quinazolone derivatives, and associated pharmaceutically acceptable salts thereof, and associated compositions, methods for use as therapeutic agents, and methods of preparation thereof.

BACKGROUND OF THE INVENTION

Alpha-1-adrenergic receptors are G-protein coupled transmembrane receptors that mediate various actions of the sympathetic nervous system through the binding of the catecholamines, epinephrine and norepinephrine (NE). Currently, several subtypes of the alpha-1 adrenergic receptors are known to exist for which the genes have been cloned: alpha-1A (previously known as alpha-1C), alpha-1B and alpha-1D. Recently the existence of a low affinity alpha-1 adrenoceptor for prazosin named alpha-1L, in human prostate has been determined. However, the gene for the alpha-1L-adrenergic receptor subtype has yet to be cloned.

Alpha-1 adrenoceptor antagonists have been shown in numerous clinical studies to be effective in relieving the symptoms associated with benign prostatic hypertrophy, also known as benign prostatic hyperplasia (BPH), an illness typically affecting men over fifty. The symptoms of the condition include, but are not limited to increased difficulty in urination and sexual dysfunction. Drugs such as prazosin, indoramin, doxazosin and tamsulosin are in common clinical use for BPH, and are effective in reducing both "obstructive" symptoms (eg. weak stream) and "irritative" symptoms (eg. urinary urge and frequency, nocturia). However, these compounds are all non-subtype-selective, and have the potential to cause significant side-effects, particularly cardiovascular effects such as postural hypotension, dizziness and syncope, and CNS effects including aesthenia (tiredness). These effects can limit dosing and thus clinical efficacy in reducing symptoms associated with BPH.

Pharmacological studies resulting in the subdivision of alpha-1 adrenoceptors into alpha-1A, alpha-1B and alpha-1D adrenoceptors have led to the suggestion that development of subtype-selective antagonists may allow improved symptomatic treatment of BPH/unstable bladder with a lower incidence of dose-limiting side-effects. Recently, much interest has been focused on the role of the alpha-1A adrenoceptor subtype in BPH, as a result of studies demonstrating that this subtype predominates in the urethra and prostate of man (Price et al., *J. Urol.*, 1993, 150, 546–551; Faure et al., *Life Sci.*, 1994, 54, 1595–1605; Taniguchi et al., *Naunyn Schmiedeberg's Arch. Pharmacol.*, 1997, 355, 412–416), and appears to be the receptor mediating NE-induced smooth muscle contraction in these tissues (Forray et al., *Mol. Pharmacol.*, 1994, 45, 703–708; Hatano et al., *Br. J. Pharmacol.*, 1994; 113, 723–728; Marshall et al., *Br J.* *Pharmacol.*, 1995, 115, 781–786). The resulting smooth muscle tone is believed to contribute substantially to the total urinary outflow obstruction observed in patients with BPH (Furuya et al., *J. Urol.*, 1982, 128, 836–839), with the remaining being attributable to increased prostate mass. These observations have fuelled the hypothesis that an alpha-1A subtype-selective antagonist may, via a selective and significant decrease in outlet resistance, lead to improved pharmacotherapy for BPH.

However, it must be noted that in BPH, it is often the irritative symptoms which prompt the patient to seek treatment, and that these irritative symptoms may be present even in patients with no demonstrable obstruction (i.e. normal urine flow rates). Recently in U.S. patent application Ser. No. 09/521,185 Ford et al. have described the use of selective alpha-1B adrenoceptor antagonists for the treatment of disorders resulting in irritative bladder symptoms. The current proposal is that by combining both alpha-1A and alpha-1B subtype selectivity in a drug molecule, it would be possible to reduce both obstructive and irritative symptoms in patients with BPH. The lack of alpha-1D adrenoceptor antagonism is expected to lead to reduced or fewer side effects than those associated with the use of non-subtype-selective agents.

All publications, patents, and patent applications cited herein, whether supra or infra, are each hereby incorporated by reference in its entirety.

DESCRIPTION OF THE RELATED ART

U.S. Pat. No. 3,960,861 and U.S. Pat. No. 4,044,136 (Danilewitz et al.) refers to certain 2-amino- and 4-amino-quinazoline derivatives as anti-hypertensive agents.

U.S. Pat. No. 4,686,228 (Campbell et al.) refers to certain 4-amino-quinazoline derivatives as antihypertensive agents.

U.S. Pat. No. 6,103,738 (Collins et al.) refers to certain quinoline and quinazoline compounds useful in the treatment of benign prostatic hypertrophy.

BE 678,216 (assigned to Pfizer) refers to certain quinazolone derivatives used as hypertensive agents.

PCT Published Application WO 98/30560 (assigned to Pfizer) refers to certain quinoline and quinazoline compounds useful in the treatment of benign prostatic hyperplasia.

GB Patent Application No. 1,062,357 (assigned to Pfizer) refers to certain quinazolone derivatives used as anti-hypertensive agents.

DE Patent Application No. 2,757,925 A1 (assigned to Bayer) refers to certain diazabicyclo-1,2,4-benzothiadiazines used as anti-hypertensive and possibly as antidiabetic agents.

Gupta et al., *J. Med. Chem.*, 1968, 11(2), 392–395 refers to syntheses of substituted quinazolones, and quinazolines, and triazepino- and triazocinoquinazolones, exhibiting CNS-depressant activity.

Leonardi et al., *J. Med. Chem.*, 1999, 42, 427–437 refers to structure activity relationship studies on 2,4-diamino-6,7-dimethoxyquinazoline as alpha-1 adrenoceptor antagonists.

Menziani et al., *Bioorg. Med. Chem*, 1999, 7(11), 2437–2451 refers to structure-activity relationship analysis of alpha-1 adrenergic receptor antagonists.

Villalorgo et al., *Synlett*, 1998, 12, 1405–1407, refers to solid phase state syntheses of 3H-quinazolin-4-one derivatives.

Wollweber et al., *Arzneim.-Forsch.*, 1981, 31(2), 279–88 refers to 3-amino-2H-1,2,4-benzothiadiazine-1,1-dioxides with antihypertensive and possibly diabetogenic activity.

All publications, patents, and patent applications cited herein, whether supra or infra, are each hereby incorporated by reference in its entirety.

SUMMARY OF THE INVENTION

This invention relates to compounds comprising Formula I:

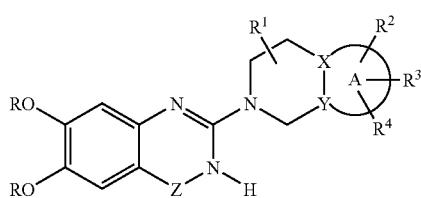

wherein:

X is carbon or nitrogen; Y is carbon; and X-Y considered together are two adjoining atoms of the ring A, said ring being a fused aromatic ring of five to six atoms per ring optionally incorporating one to two heteroatoms per ring, chosen from N, O, or S;

Z is —C(O)— or —S(O)$_2$—;

R is lower alkyl;

$R^1$ is hydrogen; lower alkyl;

aryl, arylalkyl, arylaminocarbonyl, wherein the aryl group is optionally substituted with one to two substituents selected from the group consisting of lower alkyl, halo, cyano, and lower alkoxy;

heteroaryl or heteroarylalkyl, wherein the heteroaryl group is optionally substituted with one to two substitutents selected from the group consisting of lower alkyl, halogen, cyano, and lower alkoxy;

$R^2$, $R^3$, and $R^4$ are each independently in each occurrence hydrogen; lower alkyl; cycloalkyl or cycloalkylalkyl, wherein the cycloalkyl group is optionally substituted with one or more substitutents selected from the group consisting of hydroxy, cyano, lower alkyl, lower alkoxy, halogen-loweralkoxy, alkylthio, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, alkylcarbonylamino, and phenyl optionally substituted with one or two substitutents selected from the group consisting of lower alkyl, halogen, cyano, and lower alkoxy;

aryl or arylalkyl, wherein the aryl group is optionally substituted with one or more substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino, or two adjacent atoms of the aryl ring can be substituted with a methylenedioxy or ethylenedioxy group;

heterocyclyl or heterocyclylalkyl, wherein the heterocyclyl group is optionally substituted with one or more substituents selected from the group consisting of hydroxy, hydroxyalkyl, oxo, cyano, cyanoalkyl, lower alkyl, lower alkoxy, alkoxyalkyl, halogen-lower alkoxy, alkylthio, halogen, haloalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino;

heteroaryl or heteroarylalkyl, wherein the heteroaryl group is optionally substituted with one or more substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino;

hydroxy; hydroxyalkyl; alkoxy; alkoxyalkyl; halo; haloalkyl; cyano; cyanoalkyl; —(CH$_2$)$_{0-3}$NR'R"; —C(NH)—NR'R"; —N—C(NR')—R"; —N═CR'—NR'R"; —SO$_2$NR'R"; —NSO$_2$R'; —C(O)R'; —C(O)NR' R"; or —NC(O)R';

with the proviso that if A is a benzene ring, at least one of $R^2$, $R^3$ or $R^4$ is not hydrogen; or $R^2$ and $R^3$, if adjacent, taken together with the carbons to which they are attached may also form a 5- to 7-membered aromatic, saturated or unsaturated ring, optionally incorporating one or two ring heteroatoms chosen from N, O, or S, and optionally substituted with one or two substitutents selected from the group consisting of lower alkyl, halo, cyano, alkylthio, and lower alkoxy; and R' and R" are independently in each occurrence hydrogen; lower alkyl; substituted lower alkyl; hydroxyalkyl; alkoxyalkyl; cycloalkyl, wherein the cycloalkyl group optionally substituted with one or more substituents selected from the group consisting of hydroxy, cyano, lower alkyl, lower alkoxy, halo-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and phenyl;

aryl or arylalkyl, wherein the aryl group is optionally substituted with one or more substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonyl-amino, and arylcarbonylamino, or two adjacent atoms of the aryl ring can be substituted with a methylenedioxy or ethylenedioxy group;

heteroaryl or heteroarylalkyl, wherein the heteroaryl group is optionally substituted with one or more substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkyl-sulfonylamino, arylsulfonylamino, alkylaminocarbonyl, arylaminocarbonyl, alkylcarbonylamino, and arylcarbonylamino;

heterocyclyl or heterocyclylalkyl, wherein the heterocyclyl group is optionally substituted with one or more substituents selected from the group consisting of hydroxy, oxo, cyano, cyanoalkyl, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino;

or R' and R" together with the nitrogen they are attached to may also form a 5- to 7-membered ring, optionally incorporating one additional ring heteroatom chosen from N, O, or S, wherein said ring can be substituted with one or two substitutents selected from the group consisting of lower alkyl, halogen, cyano, and lower alkoxy;

or prodrugs, individual isomers, racemic or non-racemic mixtures of isomers, or salts or solvates thereof.

Another aspect of this invention relates to pharmaceutical compositions containing a therapeutically effective amount of at least one compound of Formula I, or individual isomers, racemic or non-racemic mixtures of isomers, or pharmaceutically acceptable salts or solvates thereof, in admixture with at least one suitable carrier. In a more preferred embodiment, the pharmaceutical composititions are suitable for administration to a subject having a disease state that is alleviated by treatment with an antagonist combining alpha-1A and alpha-1B subtype selectivity.

Another aspect of this invention relates to the use of compounds of Formula I in the treatment of a subject having a disease state that is alleviated by treatment with an antagonist combining alpha-1A and alpha-1B subtype selectivity, which comprises administering to such a subject a therapeutically effective amount of at least one compound of Formula I, or in a more preferred embodiment this invention relates to methods of treating a subject having a disease state comprising disorders of the urinary tract, and in another embodiment the invention relates to methods of treating a subject having a disease state comprising pain.

In another aspect, the invention further relates to a process for preparing compounds of the general Formula I, which process comprises:

reacting a compound of general Formula II;

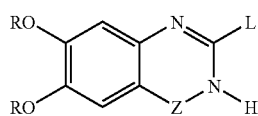

wherein L is a leaving group,
with a compound of general Formula III:

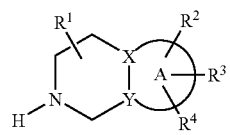

optionally in the presence of a base as described below in the specification, to provide a compound of general Formula I

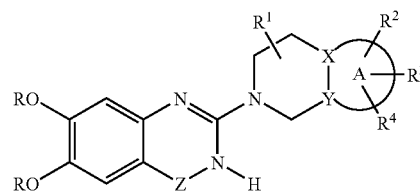

wherein R, $R^1$, $R^2$, $R^3$, $R^4$, X, Y, Z, and A are as defined herein.

PREFERRED EMBODIMENTS

Among the family of compounds of the present invention, a preferred embodiment includes compounds wherein X is carbon, and another preferred embodiment includes compounds wherein X is nitrogen.

Another preferred embodiment includes compounds wherein $R^1$ is hydrogen; a preferred subgroup within this category includes the compounds wherein X is carbon, and A is a fused aryl group, and yet another subgroup includes the compounds wherein A is a fused benzene group. Another preferred subgroup of this embodiment includes compounds wherein $R^1$ is hydrogen, X is carbon, and A is a fused heteroaryl ring, and a more preferred subgroup within this category includes the compounds wherein $R^1$ is hydrogen, X is carbon, and A is a fused pyrimidine ring.

Another preferred embodiment includes compounds wherein $R^1$ is hydrogen, X is carbon, and A is a fused pyrrole ring; a preferred subgroup within this category includes compounds wherein $R^2$ and $R^3$ taken together with the carbons to which they are attached may also form a fused benzene ring optionally substituted with one or two substitutents selected from lower alkyl, halo, haloalkyl, cyano, alkylthio, or lower alkoxy.

Another preferred embodiment includes compounds wherein $R^1$ is hydrogen, X is carbon, and A is a fused pyridine ring.

Another preferred embodiment includes compounds wherein $R^1$ is hydrogen, X is carbon, and A is a fused imidazole ring, and another preferred embodiment includes compounds wherein $R^1$ is hydrogen, X is nitrogen, and A is a fused imidazole ring.

Another preferred embodiment includes a group of compounds wherein $R^1$ is hydrogen, and $R^2$ is —$(CH_2)_{0-3}$NR'R" or —$SO_2$NR'R", wherein R' and R" are independently in each occurrence hydrogen, lower alkyl, substituted lower alkyl, cycloalkyl, aryl, arylalkyl, heteroaryl, heteroarylalkyl, and R' and R" together with the nitrogen they are attached may also form a 5- to 7-membered ring, optionally incorporating one additional ring heteroatom chosen from N, O, or S.

Another preferred embodiment includes compounds wherein X is carbon and A is a fused benzene ring, and $R^2$ is —$(CH_2)_{0-3}$NR'R" or —$SO_2$NR'R", wherein R' and R" are independently in each occurrence hydrogen, lower alkyl, substituted lower alkyl, cycloalkyl, aryl, arylalkyl, heteroaryl, heteroarylalkyl, and R' and R" together with the nitrogen they are attached may also form a 5- to 7-membered ring, optionally incorporating one additional ring heteroatom chosen from N, O, or S; and within this category one subgroup includes compounds wherein Z is —C(O)—, and another subgroup includes compounds wherein Z is —S(O)₂—.

In another embodiment X is carbon, A is a fused benzene ring, and R² is selected from the groups —C(NH)—NR'R", —N—C(NR')—R", and —N=CR'—NR'R", wherein R' and R" are independently in each occurrence hydrogen, lower alkyl, substituted lower alkyl, cycloalkyl, aryl, arylalkyl, heteroaryl, heteroarylalkyl, or R' and R" together with the nitrogen they are attached may also form a 5- to 7-membered ring, optionally incorporating one additional ring heteroatom chosen from N, O, or S, and within this category one subgroup includes compounds wherein Z is —C(O)—.

Another embodiment includes compounds wherein R¹ is hydrogen, X is carbon, A is a fused benzene group and R² is aryl or heteroaryl.

Another embodiment includes compounds wherein R¹ is hydrogen, X is carbon, A is a fused benzene group and R² is alkoxy, cyano, or cyanoalkyl.

Another preferred embodiment includes compounds wherein R¹ is hydrogen, and R² is —(CH₂)₀₋₃NR'R" or —SO₂NR'R", wherein R' and R" are independently in each occurrence hydrogen, lower alkyl, substituted lower alkyl, cycloalkyl, aryl, arylalkyl, heteroaryl, heteroarylalkyl, and R' and R" together with the nitrogen they are attached may also form a 5- to 7-membered ring, optionally incorporating one additional ring heteroatom chosen from N, O, or S; X is carbon and A is a fused pyrimidine ring; within this category one subgroup includes compounds wherein Z is —C(O)—, and another subgroup includes compounds wherein Z is —S(O)₂—. In another embodiment R² is —NR'R", and wherein R' and R" together with the nitrogen they are attached may also form a 5- to 7-membered ring, optionally incorporating one additional ring heteroatom chosen from N, O, or S.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon radical, having from one to six carbon atoms inclusive, unless otherwise indicated. Examples of lower alkyl radicals include, but are not limited to, methyl, ethyl, propyl, isopropyl, 1-ethylpropyl, sec-butyl, tert-butyl, n-butyl, n-pentyl, n-hexyl, and the like.

"Lower alkyl" means the monovalent linear or branched saturated hydrocarbon radical, having from one to six carbon atoms inclusive, unless otherwise indicated. Examples of lower alkyl radicals include, but are not limited to, methyl, ethyl, propyl, isopropyl, 1-ethylpropyl, sec-butyl, tert-butyl, n-butyl, n-pentyl, n-hexyl, and the like.

"Substituted lower alkyl" means the lower alkyl as defined herein, including one to three substituents, preferably one substituent such as hydroxyl, alkoxy, amino, amido, carboxyl, acyl, halogen, cyano, thiol, cycloalkyl, aryl, heterocyclyl, and heteroaryl. These groups may be attached to any carbon atom of the lower alkyl moiety. Examples of substituted lower alkyl radicals include, but are not limited to, acetic acid 1-methyl-2-ylethylester, methoxyethyl, 4-hydroxy-butyl, 2-amino-3-phenyl-propyl, 4-hydroxy-2,2-dimethyl butyl, 4-hydroxy-3,3-dimethyl-butyl, 4-amino-3,3-dimethyl-butyl, trifluorobutyl and the like.

"Lower alkoxy" means the radical —O—R, wherein R is a lower alkyl radical as defined herein. Examples of alkoxy radicals include, but are not limited to, methoxy, ethoxy, isopropoxy, and the like.

"Aryl" means the monovalent aromatic carbocyclic radical consisting of one individual ring, or one or more fused rings in which at least one ring is aromatic in nature, which can optionally be substituted with one or more, preferably one or two, substituents selected from hydroxy, cyano, lower alkyl, lower alkoxy, halo-lower alkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, indanyl, tert-butyl-phenyl, 1,3-benzodioxolyl, 2,3-dihydrobenzo[1,4]dioxinyl, and the like.

"Arylalkyl" (or "aralkyl") means the radical R'R"—, wherein R' is an aryl radical as defined herein, and R" is a lower alkylene radical as defined herein. Examples of arylalkyl radicals include, but are not limited to, benzyl, phenylethyl, 3-phenylpropyl, and the like.

"Cycloalkyl" means the monovalent saturated carbocyclic radical consisting of one or more rings, preferably one or two rings, of three to eight carbons per ring, which can optionally be substituted with one or more, preferably one or two substitutents, selected from hydroxy, cyano, lower alkyl, lower alkoxy, halo-lower alkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino , alkylaminocarbonyl, arylaminocarbonyl, alkylcarbonylamino, arylcarbonylamino, and phenyl optionally substituted with one or two substituents selected from lower alkyl, halogen, cyano or lower alkoxy, unless otherwise indicated. Examples of cycloalkyl radicals include, but are not limited to, cyclopropyl, cyclobutyl, 3-ethylcyclobutyl, cyclopentyl, cyclohexyl, 4-phenylcyclohexyl, and the like.

"Heteroaryl" means the monovalent aromatic cyclic radical having one or more rings, preferably one to three rings, of four to eight atoms per ring, incorporating one or more heteroatoms, preferably one or two, within the ring (chosen from nitrogen, oxygen, or sulfur), which can optionally be substituted with one or more, preferably one or two substituents selected from hydroxy, cyano, lower alkyl, lower alkoxy, halo-loweralkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heteroaryl radicals include, but are not limited to, imidazolyl, oxazolyl, thiazolyl, pyrazinyl, pyrimidinyl, thienyl, furanyl, pyridinyl, pyrrolinyl, quinolinyl, isoquinolinyl, benzofuryl, benzothiophenyl, benzothiopyranyl, benzimidazolyl, benzoxazolyl, benzothiazolyl, benzopyranyl, indazolyl, indolyl, isoindolyl, quinolinyl, isoquinolinyl, naphthyridinyl, benezenesulfonyl-thienyl, and the like.

"Heterocyclyl" means the monovalent saturated or partially unsaturated cyclic radical, consisting of one or more rings, preferably one to two rings, of three to eight atoms per ring, incorporating one or more ring heteroatoms (chosen from N, O or $S(O)_{0-2}$), and optionally which can optionally be substituted with one or more, preferably one or two substituents selected from hydroxy, hydroxyalkyl, oxo, cyano, lower alkyl, lower alkoxy, halo-loweralkoxy, alkylthio, halo, haloalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, morpholinyl, piperazinyl, piperidinyl, pyrrolidinyl, tetrahydropyranyl, thiomorpholinyl, and the like. Further examples of heterocyclic radicals include 2,4,dixo-1H-pyrimidyl; 4,5-dihydro-3H-pyrrolyl; 3,4,5,6-tetrahydro-2-pyridinyl; or 5,6-dihydro-2H-[1,4]thiazin-3-yl.

"Halogen", "halo", or "halide" means the radical fluoro, bromo, chloro, and/or iodo.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Optionally substituted" means that a group may or may not be substituted with one or more, preferably one or two substitutents independently selected from the specified group. For example phenyl optionally substituted with lower alkyl, alkoxy, halo or cyano means that the phenyl group may or may not be substituted at any position with one or more, preferably one or two substituents independently selected from the group lower alkyl, alkoxy, halo or cyano.

"Leaving group" means the group with the meaning conventionally associated with it in synthetic organic chemistry, i.e., an atom or group displaceable by a nucleophile. Examples of leaving groups include, but are not limited to, halogen, alkylsulfonyl or arylsulfonyloxy, such as methanesulfonyloxy, ethanesulfonyloxy, methylthiolate, benzenesulfonyloxy, tosyloxy, and, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively includes groups protected as acetates, haloalkyl carbonates, phenyl sulfonates, alkylsilyl ethers, heterocyclyl ethers, benzyl ethers, and methyl or alkyl ethers, and the like. Protective or blocking groups for carboxyl groups are similar to those described for hydroxyl groups, preferably tert-butyl, benzyl or methyl esters. Examples of protecting groups can be found in T. W. Greene et al., *Protective Groups in Organic Chemistry*, (J. Wiley, $2^{nd}$ ed. 1991) and Harrison et al., *Compendium of Synthetic Organic Methods*, Vols 1–8 (J. Wiley and Sons 1971–1996).

"Amino-protecting group" means the protecting group that refers to those organic groups intended to protect the nitrogen atom against undesirable reactions during synthetic procedures and includes, but is not limited to, benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by mild acids in the case of BOC, e.g., trifluoroacetic acid or hydrochloric acid in ethyl acetate; or by catalytic hydrogenation with e.g. 10% palladium on carbon (10% Pd/C), palladium hydroxide, palladium acetate, etc., preferably 10% Pd/C, in the presence of ammonium formate and in an appropriate solvent, typically an alcohol (e.g., ethanol, methanol, isopropanol, any appropriate mixture of alcohols, etc.) in the case of CBZ.

"Deprotection" or "deprotecting" means the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are nonsuperimposable mirror images are termed "enantiomers", or sometimes optical isomers. A carbon atom bonded to four nonidentical substituents is termed a "chiral center".

"Chiral compound" means a compound with one or more chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When chiral centers are present, the stereoisomers may be characterized by the absolute configuration (R or S) of the chiral centers. Absolute configuration refers to the arrangement in space of the substituents attached to a chiral center. The substituents attached to a chiral center under consideration are ranked in accordance with the *Sequence Rule of Cahn,* Ingold and Prelog. (Cahn et al. *Angew. Chem. Inter.,* 1966, Edit., 5, 385; errata 511; Cahn et al. *Angew. Chem.,* 1966, 78, 413; Cahn and Ingold, *J. Chem. Soc.* (London), 1951, 612; Cahn et al., *Experientia,* 1956, 12, 81; Cahn, *J., Chem. Educ.,* 1964, 41, 116).

"Atropic isomers" means the isomers owing their existence to restricted rotation caused by hindrance of rotation of large groups about a central bond.

"Tautomers" refers to compounds whose structures differ markedly in arrangement of atoms, but which exist in easy and rapid equilibrium. It is to be understood that compounds of Formula I may be depicted as different tautomers.

For example, compounds of Formula I wherein Z is —C(O)—, may be depicted in the following tautomer forms:

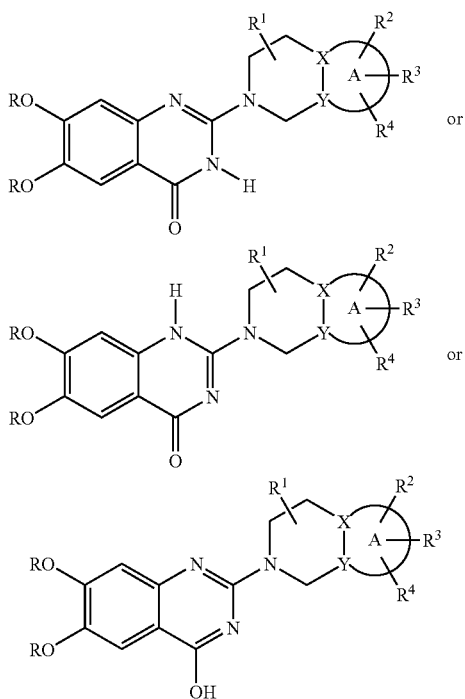

Compounds of Formula I wherein Z is —S(O)$_2$—, may be depicted in the following tautomer forms:

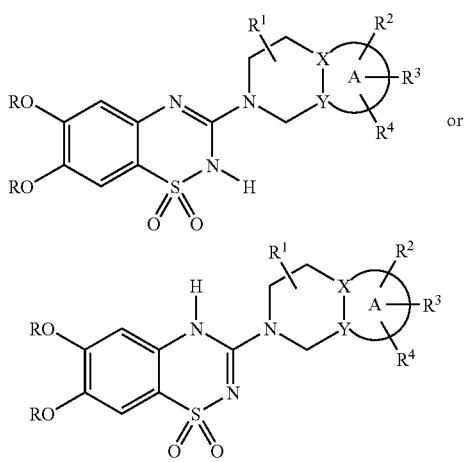

Compounds of Formula I may also contain other groups that exist in tautomeric equilibrium. For example some of the compounds contain an imidazolin-2-yl amino group which would be in equilibrium with the imidazolin-2-ylidenamino group:

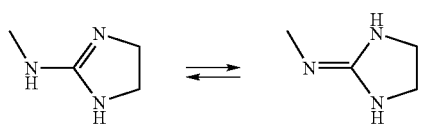

It should also be understood that when compounds have tautomeric forms, all tautomeric forms are intended to be within the scope of the invention, and the naming of the compounds does not exclude any tautomer form.

"Substantially pure" means at least about 80 mole percent, more preferably at least about 90 mole percent, and most preferably at least about 95 mole percent of the desired enantiomer or stereoisomer is present.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Acceptable salt" of a compound means salt that is pharmaceutically acceptable, as defined herein, and that possesses the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, 2,2,2-trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred acceptable salts are the salts formed from hydrochloric acid, 2,2,2-trifluoroacetic acid, dibenzoyl-L-tartaric acid, and phosphoric acid. It should be understood that all references to acceptable salts include solvent addition forms (solvates) or crystal forms (polymorphs) as defined herein, of the same acid addition salt.

"Crystal forms" (or "polymorphs") means crystal structures in which a compound can crystallize in different crystal packing arrangements, all of which have the same elemental composition. Different crystal forms usually have different X-ray diffraction patterns, infrared spectra, melting points, density, hardness, crystal shape, optical and electrical properties, stability and solubility. Recrystallization solvent, rate of crystallization, storage temperature, and other factors may cause one crystal form to dominate.

"Solvate" means solvent addition form that contains either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action,* by Richard B. Silverman, Academic Press, San Diego, 1992. Chapter 8: "Prodrugs and Drug delivery Systems" pp.352–401; *Design of Prodrugs,* edited by H. Bundgaard, Elsevier Science, Amsterdam, 1985; *Design of Biopharmaceutical Properties through Prodrugs and Analogs,* Ed. by E. B. Roche, American Pharmaceutical Association, Washington, 1977; and *Drug Delivery Systems,* ed. by R. L. Juliano, Oxford Univ. Press, Oxford, 1980.

"Subject" means mammals and non-mammals. Mammals means any member of the *Mammalia* class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, reptiles, and the like.

"Therapeutically effective amount" means an amount of a compound that, when administered to a subject for treating a disease state, is sufficient to effect such treatment for the disease state. The "therapeutically effective amount" will vary depending on the compound, and disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. In one preferred embodiment, a pharmacological effect means that primary indications of the subject being treated are prevented, alleviated, or reduced. For example, a pharmacological effect would be one that results in the prevention, alleviation or reduction of primary indications in a treated subject. In another preferred embodiment, a pharmacological effect means that disorders or symptoms of the primary indications of the subject being treated are prevented, alleviated, or reduced. For example, a pharmacological effect would be one that results in the prevention or reduction of primary indications in a treated subject.

"Disease state" means any disease, condition, symptom, or indication.

"Treating" or "treatment" of a disease state includes:
(1) preventing the disease state, i.e. causing the clinical symptoms of the disease state not to develop in a subject that may be exposed to or predisposed to the disease state, but does not yet experience or display symptoms of the disease state.
(2) inhibiting the disease state, i.e., arresting the development of the disease state or its clinical symptoms, or
(3) relieving the disease state, i.e., causing temporary or permanent regression of the disease state or its clinical symptoms.

"Antagonist" means a molecule such as a compound, a drug, an enzyme inhibitor, or a hormone, that diminishes or prevents the action of another molecule or receptor site.

"Disorders of the urinary tract" or "uropathy" used interchangeably with "symptoms of the urinary tract" means the pathologic changes in the urinary tract. Symptoms of the urinary tract include overactive bladder (also known as detrusor hyperactivity), outlet obstruction, outlet insufficiency, pelvic hypersensitivity. incontinence, benign prostatic hypertrophy or hyperplasia (BPH), prostatitis, detrusor hyperreflexia, urinary frequency, nocturia, urinary urgency, pelvic hypersensitivity, urge incontinence, urethritis, prostatodynia, cystitis, idiopathic bladder hypersensitivity, sexual dysfunction, and the like.

"Overactive bladder" or "Detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Outlet obstruction" includes, but is not limited to, benign prostatic hypertrophy or benign prostatic hyperplasia (BPH), urethral stricture disease, tumors and the like. It is usually symptomatically manifested as obstructive (low flow rates, difficulty in initiating urination, and the like), or irritative (urgency, suprapubic pain, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to, pelvic pain, interstitial (cell) cystitis, prostadynia, prostatitis, vulvadynia, urethritis, orchidalgia, and the like. It is symptomatically manifested as pain, inflammation or discomfort referred to the pelvic region, and usually includes symptoms of overactive bladder.

"Sexual dysfunction" means the inability of achieving a normal sexual response in both males and females, and includes male erectile dysfunction (MED) and female sexual dysfunction (FSD).

"Disease states associated with the Central Nervous System (CNS)" or "CNS disease states" mean neurological and/or psychiatric changes in the CNS, e.g., brain and spinal cord, which manifest in a variety of symptoms. Examples of CNS disease states include, but are not limited to, migraine headache; cerebrovascular deficiency; psychoses including paranoia, schizophrenia, attention deficiency, and autism; obsessive/compulsive disorders including anorexia and bulimia; posttraumatic stress disorders, sleep disorders, convulsive disorders including epilepsy and withdrawal from addictive substances; cognitive diseases including Parkinson's disease and dementia; and anxiety/depression disorders such as anticipatory anxiety (e.g., prior to surgery, dental work and the like), depression, mania, seasonal affective disorder (SAD), and convulsions and anxiety caused by withdrawal from addictive substances such as opiates, benzodiazepines, nicotine, alcohol, cocaine, and other substances of abuse; and improper thermoregulation.

Throughout the application the following abbreviations are used with the following meanings:

BPH Benign prostatic hypertrophy or benign prostatic hyperplasia
CNS Central nervous system
DMF N,N-Dimethylformamide
DMSO Dimethylsulfoxide
EtOAc Ethyl Acetate
Hal Halogen or halide
L Leaving group
P Protective group
THF Tetrahydrofuran Nomenclature The naming and numbering of the compounds of this invention is illustrated below:

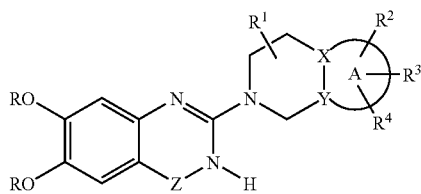

In general, the nomenclature used in this Application is based on AUTONOM™ v.4.0, a Beilstein Institute computerized system for the generation of IUPAC systematic nomenclature.

For example, a compound of Formula I wherein R is methyl, $R^1$, $R^3$, and $R^4$ are hydrogen, $R^2$ is 4-methylpiperazin-1-yl, X-Y is —C=C—, Z=C(O), and A is a fused pyrimidine group is named 6,7-dimethoxy-2-[4-(4-methylpiperazin-1-yl)-5,8-dihydro-6H-pyrido[3,4-d]pyrimidin-7-yl]-3H-quinazolin-4-one.

Similarly, a compound of Formula I wherein R is methyl, $R^1$, $R^3$, and $R^4$ are hydrogen, $R^2$ is phenyl, X-Y is —C=C—, Z=C(O), and A is a fused imidazole ring is named 6,7-dimethoxy-2-(1-phenyl-1,4,6,7-tetrahydro-imidazo[4,5-c]pyridin-5-yl)-3H-quinazolin-4-one.

Similarly, a compound of Formula I wherein R is methyl, $R^1$, $R^3$, and $R^4$ are hydrogen, $R^2$ is phenyl, X-Y is —N—C—, Z=C(O), and A is a fused imidazole ring is named 6,7-dimethoxy-2-(3-phenyl-5,6-dihydro-8H-imidazo[1,5-a]pyrazin-7-yl)-3H-quinazolin-4-one.

Similarly, a compound of Formula I wherein R is methyl, $R^1$ and $R^4$ are hydrogen, $R^2$ and $R^3$ form a phenyl ring, X-Y is —C=C—, Z=C(O), and A is a fused pyrrole ring is named 6,7-dimethoxy-2-(1,3,4,9-tetrahydro-β-carbolin-2-yl)-3H-quinazolin-4-one.

Similarly a compound of Formula I wherein R is methyl, $R^1$, $R^3$,and $R^4$ are hydrogen, $R^2$ is morpholin-4-yl, X-Y is —C=C—, Z=S(O)$_2$, and A is a fused pyrimidine ring is named 6,7-dimethoxy-3-(4-morpholin-4-yl-5,8-dihydro-6H-pyrido[3,4d]pyrimidin-7-yl)-2H-benzo[1,2,4]thiadiazine-1,1-dioxide.

Many of the compounds of Formula I exist in various tautomer forms, and it should therefore be understood that various numbering schemes may be used in the naming of compounds of Formula I.

Preferred Compounds

Among compounds of the present invention set forth in the Summary of the Invention, certain compounds of Formula I, or individual isomers, racemic or non-racemic mixtures of isomers, or acceptable salt or solvate thereof, are preferred:

R is lower alkyl, preferably methyl.

$R^1$ is preferably hydrogen or alkyl, and more preferably hydrogen.

$R^2$ is preferably hydrogen, alkyl, alkoxy, cyano, aryl, heteroaryl; —(CH$_2$)$_{0-3}$NR'R", —C(NH)—NR'R", —N—C(NR')—R", —N=CR'—NR'R", or —SO$_2$NR'R"; and more preferably —(CH$_2$)$_{0-3}$NR'R", or —SO$_2$NR'R", wherein R' and R" are independently in each occurrence hydrogen, lower alkyl, substituted lower alkyl, cycloalkyl, aryl, arylalkyl, heteroaryl, heteroarylalkyl, and R' and R" together with the nitrogen they are attached may also form a 5- to 7-membered ring, optionally incorporating one additional ring heteroatom chosen from N, O or S, or $R^2$ is —NR'R", wherein R' and R" together with the nitrogen they are attached may also form a 5- to 7-membered ring, optionally incorporating one additional ring heteroatom chosen from N, O or S. In another preferred embodiment $R^2$ is selected from the groups —C(NH)—NR'R", —N—C(NR')—R", and —N=CR'—NR'R".

$R^2$ and $R^3$ taken together are preferably an aryl or a heteroaryl group, and more preferably an aryl group, or more preferably a benzene group.

$R^3$ is preferably hydrogen, lower alkyl, lower alkoxy or halogen, more preferably hydrogen.

$R^4$ is preferably hydrogen.

X is preferably carbon or nitrogen, more preferably carbon.

X-Y considered together are preferably two adjoining atoms of a fused aromatic ring of five to six atoms per ring incorporating one to two heteroatoms per ring, chosen from N, O, or S (ring A); more preferably X-Y considered together are two adjoining atoms of a benzene, a pyrimidine, an imidazole, a pyridine or a pyrrole ring, and even more preferably of a benzene or a pyrimidine ring Z is —C(O)— or —S(O)$_2$—, preferably —C(O)—.

Other preferred compounds of the present invention include the acceptable salts of the compounds of the present invention wherein said salts are formed from hydrochloric acid or from methanesulfonic acid.

Exemplary particularly preferred compounds, or individual isomers, racemic or non-racemic mixtures of isomers, or pharmaceutically acceptable salts or solvates thereof, include:

6,7-dimethoxy-2-[5-(4-methoxy-phenyl)-3,4-dihydro-1H-isoquinolin-2-yl]-3H-quinazolin-4-one;

6,7-dimethoxy-2-[7-(4-methoxy-phenyl)-3,4-dihydro-1H-isoquinolin-2-yl]-3H-quinazolin-4-one;

6,7-dimethoxy-2-(4-morpholin-4-yl-5,8-dihydro-6H-pyrido[3,4-d]pyrimidin-7-yl)-3H-quinazolin-4-one;

6,7-dimethoxy-2-(5-pyridin-3-yl-3,4-dihydro-1H-isoquinolin-2-yl)-3H-quinazolin-4-one;

2-(4-benzylamino-5,8-dihydro-6H-pyrido[3,4-d]pyrimidin-7-yl)-6,7-dimethoxy-3H-quinazolin-4-one;

6,7-dimethoxy-2-(5-pyrrolidin-1-yl-3,4-dihydro-1H-isoquinolin-2-yl)-3H-quinazolin-4-one;

6,7-dimethoxy-2-(5-pyridin-4-yl-3,4-dihydro-1H-isoquinolin-2-yl)-3H-quinazolin-4-one;

6,7-dimethoxy-2-(5-pyrimidin-5-yl-3,4-dihydro-1H-isoquinolin-2-yl)-3H-quinazolin-4-one;

2-(6,7-dimethoxy-4-oxo-1,4-dihydro-quinazolin-2-yl)-1,2,3,4-tetrahydro-isoquinoline-7-sulfonic acid (2-pyridin-2-yl-ethyl)-amide;

2-(6,7-dimethoxy-4-oxo-3,4-dihydro-quinazolin-2-yl)-6,7-dimethoxy-1,2,3,4-tetrahydro-isoquinoline-5-carbonitrile;

6,7-dimethoxy-2-[5-(1H-pyrrol-2-yl)-3,4-dihydro-1H-isoquinolin-2-yl]-3H-quinazolin-4-one;

2-[5-(1H-imidazol-2-yl)-3,4-dihydro-1H-isoquinolin-2-yl]-6,7-dimethoxy-3H-quinazolin-4-one;

6,7-dimethoxy-2-[4-(4-methyl-piperazin-1-yl)-5,8-dihydro-6H-pyrido[3,4-d]pyrimidin-7-yl]-3H-quinazolin-4-one;

6,7-dimethoxy-2-{4-[(2-methoxy-ethyl)-methyl-amino]-5,8-dihydro-6H-pyrido[3,4-d-pyrimidin-7-yl}-3H-quinazolin-4-one;

6,7-dimethoxy-2-[5-(morpholine-4-sulfonyl)-3,4-dihydro-1H-isoquinolin-2-yl]-3H-quinazolin-4-one;

6,7-dimethoxy-2-(4-piperidin-1-yl-5,8-dihydro-6H-pyrido[3,4-d]pyrimidin-7-yl)-3H-quinazolin-4-one;

6,7-dimethoxy-2-[5-(1-morpholin-4-yl-methanoyl)-3,4-dihydro-3H-isoquinolin-2-yl]-3H-quinazolin-4-one;

6,7-dimethoxy-2-(1-phenyl-1,4,6,7-tetrahydro-imidazo[4,5-c]pyridin-5-yl)-3H-quinazolin-4-one;

2-[1-(4-chloro-phenyl)-1,4,6,7-tetrahydro-imidazo[4,5-c]pyridin-5-yl]-6,7-dimethoxy-3H-quinazolin-4-one;

6,7-dimethoxy-2-(1-naphthalen-2-yl-1,4,6,7-tetrahydro-imidazo[4,5-c]pyridin-5-yl)-3H-quinazolin-4-one;

6,7-dimethoxy-2-[1-(4-methoxy-phenyl)-1,4,6,7-tetrahydro-imidazo[4,5-c]pyridin-5-yl]-3H-quinazolin-4-one;

2-[1-(3-chloro-phenyl)-1,4,6,7-tetrahydro-imidazo[4,5-c]pyridin-5-yl]-6,7-dimethoxy-3H-quinazolin-4-one;

6,7-dimethoxy-2-(1-m-tolyl-1,4,6,7-tetrahydro-imidazo[4,5-c]pyridin-5-yl)-3H-quinazolin-4-one;

6,7-dimethoxy-2-(3-phenyl-5,6-dihydro-8H-imidazo[1,5-a]pyrazin-7-yl)-1H-quinazolin-4-one;

2-(3-cyclohexyl-5,6-dihydro-8H-imidazo[1,5-a]pyrazin-7-yl)-6,7-dimethoxy-1H-quinazolin-4-one;

6,7-dimethoxy-2-(1,3,4,9-tetrahydro-β-carbolin-2-yl)-3H-quinazolin-4-one;

6,7-dimethoxy-2-(6-methoxy-1,3,4,9-tetrahydro-β-carbolin-2-yl)-3H-quinazolin-4-one;

6,7-dimethoxy-2-(7-methylsulfanyl-1,3,4,9-tetrahydro-β-carbolin-2-yl)-3H-quinazolin-4-one;

2-(3,4-dihydro-1H-2,7,10-triaza-anthracen-2-yl)-6,7-dimethoxy-3H-quinazolin-4-one;

3-(6,7-dimethoxy-3,4-dihydro-1H-isoquinolin-2-yl)-6,7-dimethoxy-2H-benzo[1,2,4]thiadiazine 1,1-dioxide;

2-(cyclohexylamino-5,6-dihydro-8H-imidazo[1,5-a]pyrazin-7-yl)-6,7-dimethoxy-2H-benzo[1,2,4]thiadiazine-1,1-dioxide;

6,7-dimethoxy-3-(4-morpholin-4-yl-5,8-dihydro-6H-pyrido[3,4d]pyrimidin-7-yl)-2H-benzo[1,2,4]thiadiazine 1,1-dioxide;

N-[2-(6,7-dimethoxy-4-oxo-3,4-dihydro-quinazolin-2-yl)-1,2,3,4-tetrahydro-isoquinolin-5-yl]-cyclopentanecarboxamidine;

6,7-dimethoxy-2-(5-morpholin-4-ylmethyl-3,4-dihydro-1H-isoquinolin-2-yl)-3H-quinazolin-4-one;

6,7-dimethoxy-2-(5-piperidin-1-ylmethyl-3,4-dihydro-1H-isoquinolin-2-yl)-3H-quinazolin-4-one;

2-[5-(4,5-dihydro-1H-imidazol-2-ylamino)-3,4-dihydro-1H-isoquinolin-2-yl]-6,7-dimethoxy-3H-quinazolin-4-one;

N-[2-(6,7-dimethoxy-4-oxo-3,4-dihydro-quinazolin-2-yl)-1,2,3,4-tetrahydro-isoquinolin-5-yl]-cyclobutanecarboxamidine;

N-[2-(6,7-dimethoxy-4-oxo-3,4-dihydro-quinazolin-2-yl)-1,2,3,4-tetrahydro-isoquinolin-5-yl]-butyramidine;

N-[2-(6,7-dimethoxy-4-oxo-3,4-dihydro-quinazolin-2-yl)-1,2,3,4-tetrahydro-isoquinolin-5-yl]-N,N-dimethyl-formamidine;

6,7-dimethoxy-2-[5-(1-methyl-4,5-dihydro-3H-pyrrol-2-ylamino)-3,4-dihydro-1H-isoquinolin-2-yl]-3H-quinazolin-4-one; or 2-[5-(4,5-dihydro-3H-pyrrol-2-ylamino)-3,4-dihydro-1H-isoquinolin-2-yl]-6,7-dimethoxy-3H-quinazolin-4-one.

General Synthetic Reaction Schemes

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1–15; *Rodd's Chemistry of Carbon Compounds,* Elsevier Science Publishers, 1989, Volumes 1–5 and Supplementals; and *Organic Reactions,* Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about –78° C. to about 150° C., more preferably from about 0° C. to reflux, and most preferably and conveniently at about room (or ambient) temperature, e.g., about 20° C.

Schemes 1 to 10 describe methods to generate compounds of Formula I.

Scheme 1

Scheme 1 describes a method of preparing a compound of Formula I wherein X and Y are C, A is a fused benzene ring, Z is —S(O)$_2$— or —C(O)—, and R, R$^1$, R$^2$, R$^3$, R$^4$ are as defined in the Summary of the Invention.

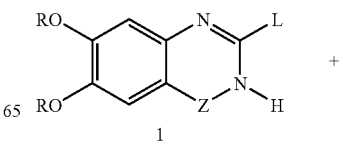

1

-continued

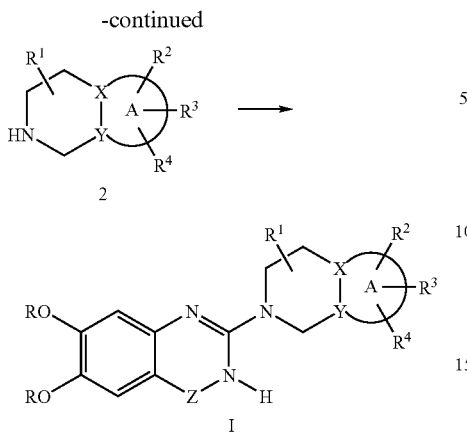

A compound of Formula 1 wherein L is a leaving group such as halogen, preferably chloro, can be prepared according to Cronin et al., *J. Med. Chem.* 1968, 11, 136–138. Reacting the free amine of Formula 2, with a compound of Formula 1 wherein L is a leaving group such as halogen, preferably chloro, in an inert solvent such as lower alkanol, methoxyethanol, DMSO or DMF, optionally in the presence of a base such as, but not limited to sodium carbonate, sodium bicarbonate, triethyl amine, tributylamine and the like, can give the compound of Formula I.

Scheme 2

Scheme 2 describes a method of preparing a compound of Formula Ia wherein A is a fused pyrimidine ring, X and Y are C, $R^2$ is —NR'R'', and R, $R^1$, $R^3$, R', R'', and Z are as defined in the Summary of the Invention.

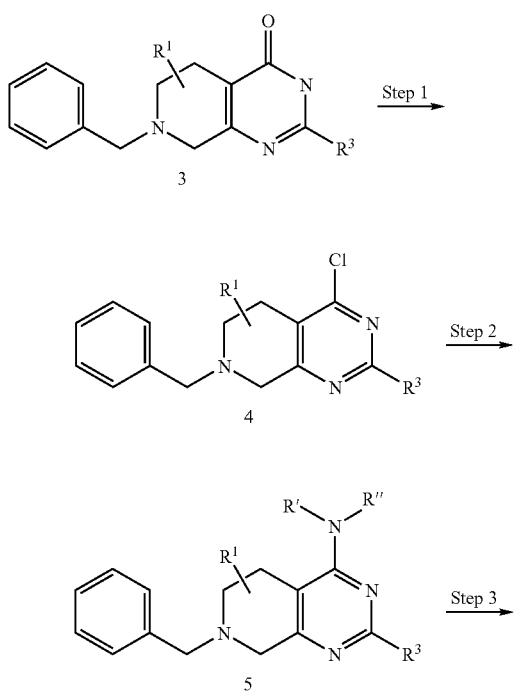

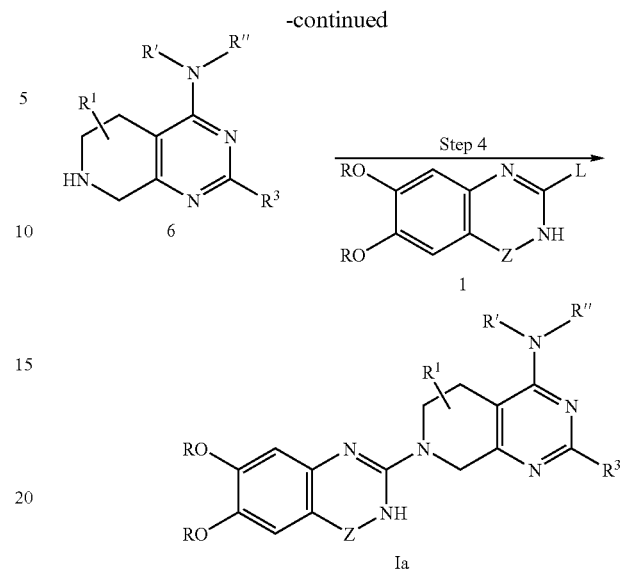

A compound of Formula 3 prepared according to Ozdowska et al., *Rocz. Chem.* 1976, 50 (10), 1771–5, can be halogenated with phosphorous oxychloride to yield the chloro derivative 4, which can be reacted with an appropriate amine in an inert solvent such as an alkanol, methoxyethanol, DMSO or DMF to yield the substituted 5,6,7,8-tetrahydro-pyrido[3,4-d]pyrimidine 5. The benzyl group of compound 5 can be removed by procedures known to one skilled in the art to yield the free base 6. A detailed description of the techniques applicable to protective groups and their removal can be found in T. W. Greene, *Protective Groups in Organic Synthesis,* Wiley and Sons, New York, 1991. For example a method of debenzylation can be carried out with a suitable catalyst (e.g., 10% palladium on carbon (Pd/C) in the presence of ammonium formate and in an appropriate solvent, typically an alcohol, preferably methanol/ethanol, at about 20° C. to about 100° C., and more preferably at reflux. Compounds of Formula Ia can be obtained by reacting the free amine 6 with a certain quinazolone derivative of Formula 1, wherein L is a leaving group, preferably a halo group, and even more preferably a chloro group, in an inert solvent such as an alkanol, preferably n-butanol or methoxyethanol, by procedures known to one skilled in the art.

Scheme 3

Scheme 3 describes a method of preparing a compound of Formula Ib wherein A is a fused imidazole ring, X is N, Y is C, and R, $R^1$, $R^2$, $R^3$, and Z are as defined in the Summary of the Invention.

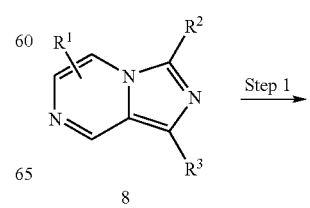

-continued

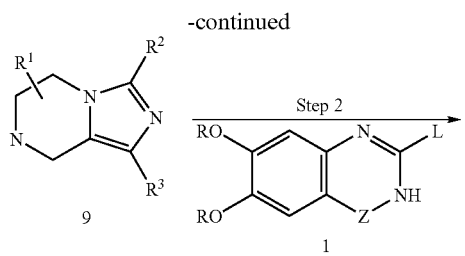

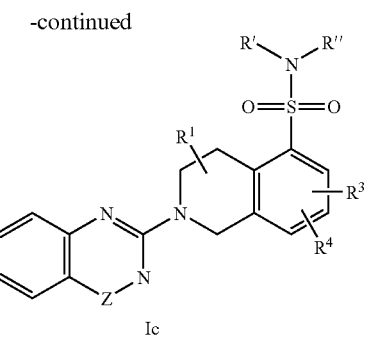

Compound 8 prepared according to Abushanab et al. *J. Heterocycl. Chem.* 1975, 12, 211 can be hydrogenated in the presence of a catalyst, preferably Adam's catalyst (platinum (IV) oxide) to give compound 9. Suitable solvents are alkanols, preferably ethanol. Compounds of Formula Ib are obtained by reaction of the free amine 9, with a certain quinazolone derivative of Formula 1, wherein L is a leaving group, preferably a halo group, and even more preferably a chloro group, as described in the previous schemes.

Scheme 4

Scheme 4 describes a method of preparing a compound of Formula Ic wherein A is a fused benzene ring, X and Y are C, $R^2$ is —$SO_2NR'R''$, and R, $R^1$, $R^3$, $R^4$, R', R'', and Z are as defined in the Summary of the Invention.

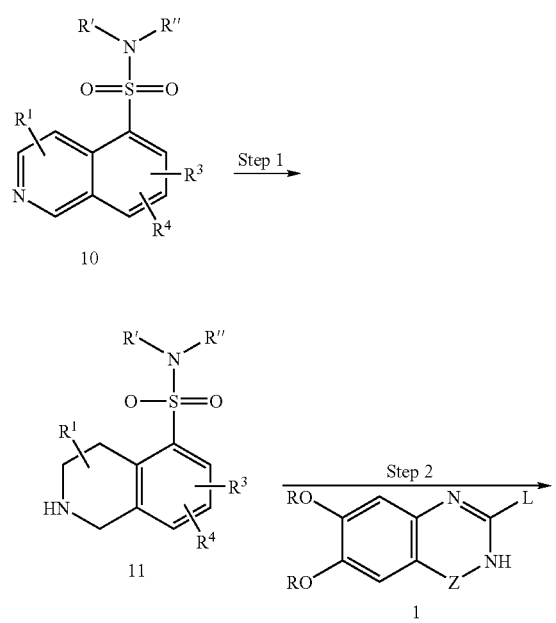

Compound 10, prepared according to Morikawa et al., *Chem. Pharm. Bull.*, 1992, 40, 770–773, can be hydrogenated in the presence of a catalyst, preferably platinum oxide to give compound 11. Suitable solvents are alkanols, preferably methanol. Compounds of Formula Ic are obtained by reaction of the free amine 11, with a certain quinazolone derivative of Formula 1, wherein L is a leaving group, preferably a halo group, and even more preferably a chloro group, as described in the previous schemes.

Scheme 5

Scheme 5 describes a method of preparing a compound of Formula Id wherein A is a fused imidazole ring, X and Y are C, $R^2$ is benzyl, and R and Z are as defined in the Summary of the Invention.

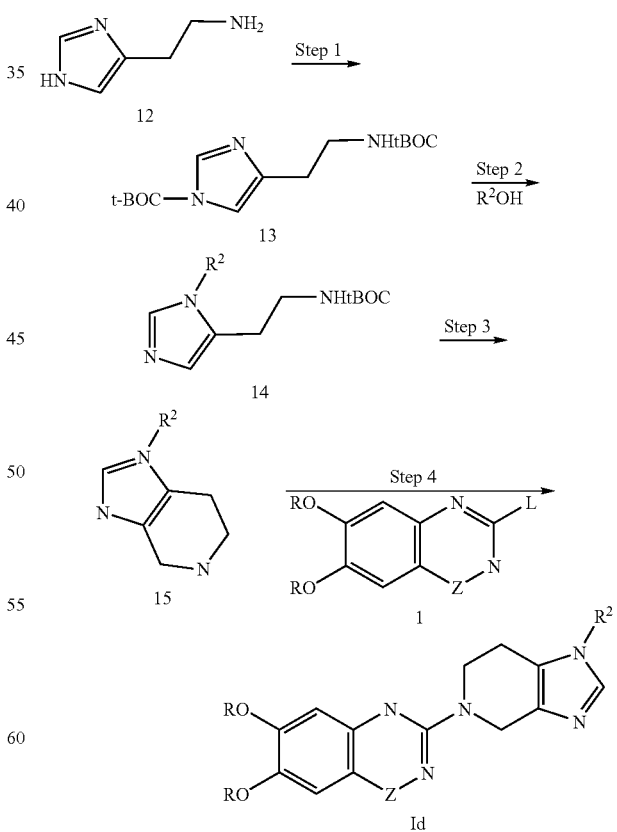

Protection of the amino groups of histamine 12 with di-tert-butyl dicarbonate under conditions well known to the artisan in the art can give the compound of Formula 13.

Formation of the amine of general Formula 14 can be effected when the protected histamine of Formula 13 is treated with a solution of benzyl alcohol and a base such as diisopropylethyl amine to which a solution of triflic anhydride in an anhydrous halogenated solvent, such as dichloromethane, has been added. Deprotection of 14 in the presence of an acid, preferably in trifluoroacetic acid in a solvent such as dichloromethane, followed by Mannich cyclization preferably with formaldehyde in the presence of an aqueous acid such as hydrochloric acid, provides amines of general Formula 15.

Compounds of Formula Id can be obtained by reaction of the free amine 15, with a certain quinazolone derivative of Formula 1, wherein L is a leaving group, preferably a halo group, and even more preferably a chloro group, as described in the previous schemes.

Scheme 6

Scheme 6 describes a method of preparing a compound of Formula Ie wherein A is a fused imidazole ring, X and Y are C, $R^2$ is phenyl and R, $R^1$, and Z are as defined in the Summary of the Invention.

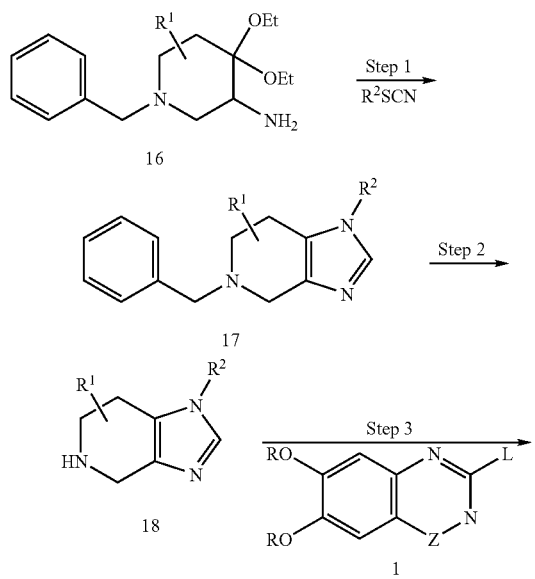

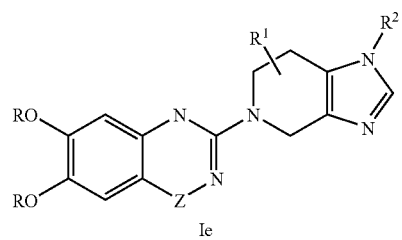

The compound of general Formula 16, prepared as described in Tetrahedron 1995, 13447–13453, can be treated with a phenyl isothiocyanate of general formula $R^2$SCN in an inert solvent such as chloroform or DMF, preferably chloroform, followed by acid catalyzed cyclization with a diluted acid such as hydrochloric acid, to the imidazolethione, which is desulfurized by methods known in the art such as by oxidation with hydrogen peroxide or by reduction with Raney Nickel to give a compound of Formula 17. Deprotection of the amino group in conditions well known in the art, such as by catalytic hydrogenation, i.e. 10% palladium on carbon (10% Pd/C), palladium hydroxide, palladium acetate, etc., in the presence of ammonium formate and in an appropriate solvent, typically an alcohol (e.g., ethanol, methanol, isopropanol, any appropriate mixture of alcohols, etc.), preferably in the presence of Pd/C can give amines of general Formula 18.

Compound of Formula Ie can be obtained by reaction of the free amine 18, with a certain quinazolone derivative of Formula 1, wherein L is a leaving group, preferably a halo group, and even more preferably a chloro group, as described in the previous schemes.

Scheme 7

Scheme 7 describes a method of preparing a compound of Formula If wherein A is a fused benzene ring, X and Y are C, $R^2$ is —$CH_2$NR'R" and R, $R^1$, $R^3$, $R^4$, R', R" and Z are as defined in the Summary of the Invention.

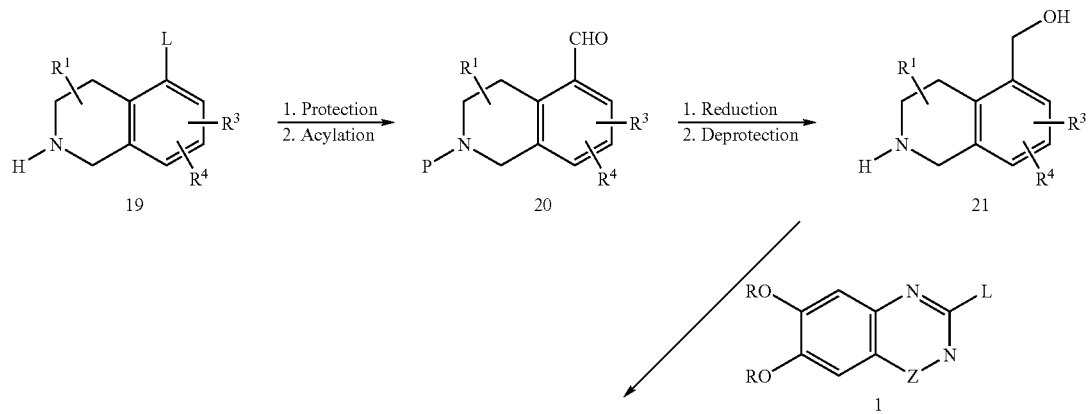

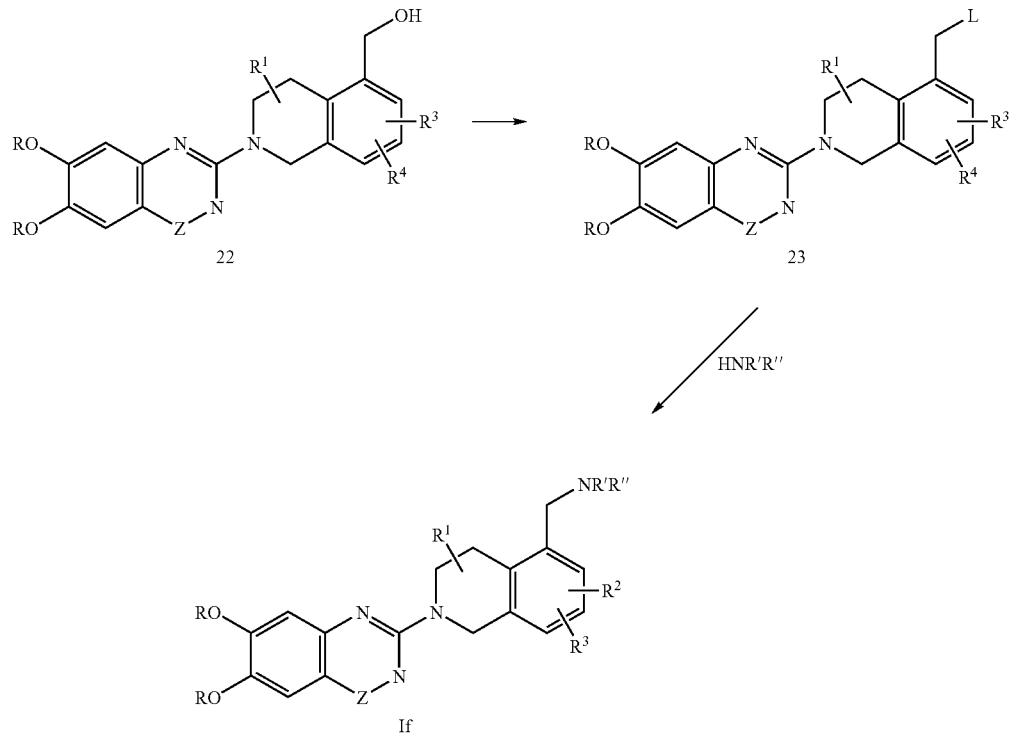

An amino compound of Formula 19 wherein L is a leaving group such as for example a halide or a triflate, is protected with a protective group such as benzyl, tert-butoxycarbonyl (BOC), carbamate, carbobenzyloxy (CBZ) under conditions well known in the art. Formylation with a N',N'-disubstituted formyl amide such as N-formylmorpholine in the presence of butyllithium can afford an aldehyde of general Formula 20. Reduction of the aldehyde with a metallic hydride such as lithium aluminum hydride or sodium borohydride, followed by deprotection by methods well known in the art such as ammonium formate and Palladium on carbon in a solvent such as methanol in the case of benzyl, can afford the alcohol of general Formula 21. Reacting the free amine of Formula 21 with a compound of Formula 1 wherein L is a leaving group such as halogen in an inert solvent can afford a compound of Formula 22. The hydroxy group can be converted in a leaving group such as a halide with halogen acids such as hydrobromic acid or with inorganic acid halides such as for example $SOCl_2$, $POBr_3$, or $POCl_3$ to afford compound 23, that can further undergo amination with an amine of general formula HNR'R" to give a compound of general Formula If, wherein $R^2$ is —$CH_2NR'R"$, and R' and R" are as defined in the specification.

Scheme 8

Scheme 8 describes a method of preparing a compound of Formula Ig wherein A is a fused benzene ring, X and Y are C, $R^2$ is —N=CR'—NR'R", and R, $R^1$, $R^3$, $R^4$, R', R" and Z are as defined in the Summary of the Invention.

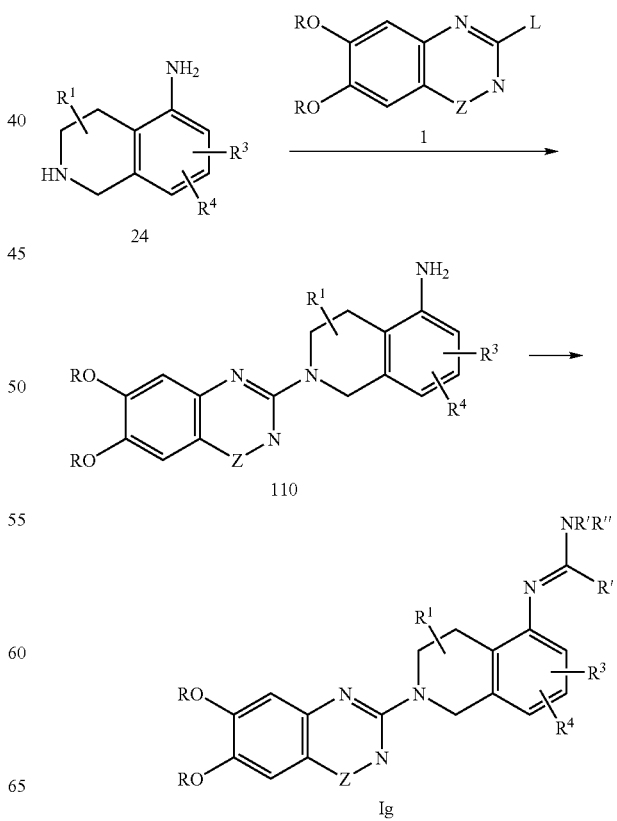

Compound of Formula Ig, wherein $R^2$ is —N=CR'—NR'R", can be prepared by reacting compound 110, with a disubstituted amide and phosphorous oxychloride. Compound 110 can be prepared from compound of general Formula 24 (prepared as described in WO 95/13274) with the quinazoline derivative of Formula 1 as described in Scheme 1.

Scheme 9

Scheme 9 describes a method of preparing a compound of Formula Ih wherein A is a fused benzene ring, X and Y are C, $R^2$ is —C(NH)—NR'R", and R, $R^1$, $R^3$, $R^4$, R', R" and Z are as defined in the Summary of the Invention.

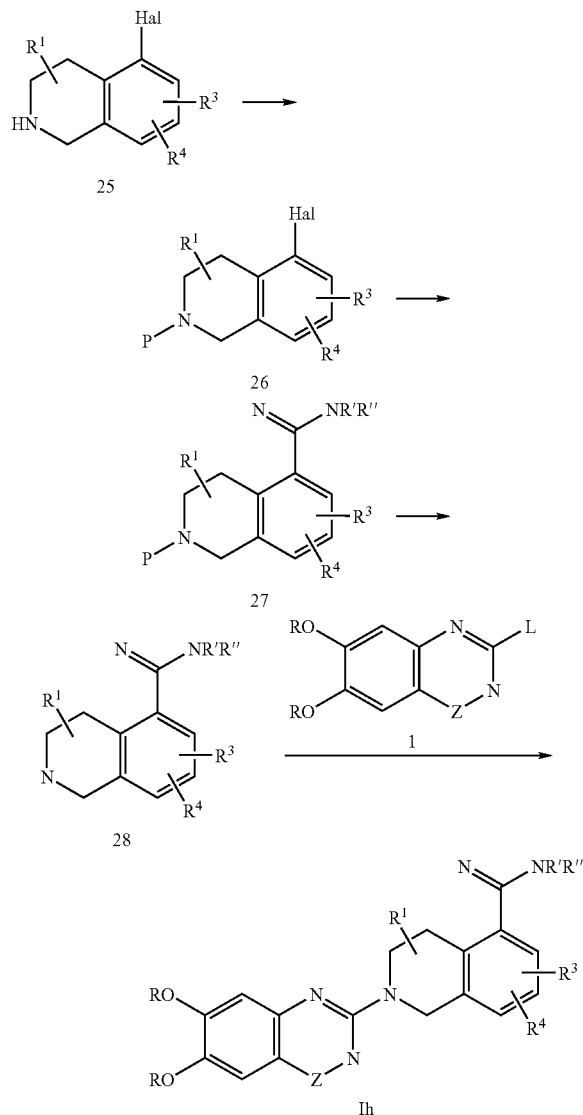

After protection of the amino group of compound of Formula 25, wherein Hal is a halogen, preferably bromo or chloro, following procedures well known in the art as described herein to afford compound of Formula 26, the halogen group can be reacted with a carbonitrile group of general formula NC—NR'R" in the presence of butylithium to give an imino amine of general Formula 27. Removal of the amino protecting group as described herein, for example with an acid, such as trifluoroacetic acid if the protective group is BOC, and coupling with the quinazoline derivative of Formula 1 can afford a compound of general Formula Ih wherein $R^2$ is —C(NH)—NR'R".

Exemplary preparations of a compound of Formula I are given in Examples 1 to 12.

General Utility

Alpha-1 adrenoceptors mediate the contractile state of smooth muscle tissue and are present in the human prostate, bladder neck and urethra. Alpha-1 adrenoceptor stimulation also produces contraction of urethral and bladder neck smooth muscle, leading to increased resistance in urinary outflow. Thus, alpha-1 adrenoceptor antagonists may be useful in preventing and treating disorders or symptoms related to uropathies, such as reduction or alleviation of urinary tract disorders, for example, overactive bladder, urinary frequency, nocturia, urinary urgency, detrusor hyperreflexia, outlet obstruction, BPH, prostatitis, urge incontinence, urethritis, idiophatic bladder hypersensitivity, sexual dysfunction, and the like.

Alpha-1 adrenoceptor antagonists have been shown in numerous clinical studies to be effective in relieving the symptoms associated with benign prostatic hypertrophy (BPH). Drugs such as prazosin, indoramin, doxazosin and the newer compound tamsulosin are in common clinical use for BPH, and are effective in reducing both "obstructive" symptoms (e.g. low flow rate) and "irritative" symptoms (e.g. urinary urge and frequency, nocturia). However, these compounds are all non-subtype-selective, and have the potential to cause significant side-effects, particularly cardiovascular effects such as postural hypotension, and CNS effects including aesthenia (tiredness). These effects can limit dosing and thus clinical efficacy in reducing symptoms associated with BPH.

Pharmacological studies resulting in the subdivision of alpha-1-adrenoceptors into alpha-1A, alpha-1B, and alpha-1D adrenoceptors have led to the suggestion that development of subtype-selective antagonists may allow improved symptomatic treatment of BPH/unstable bladder with a lower incidence of dose-limiting side-effects. Recently, much interest has focused on the role of the alpha-1A adrenoceptor subtype in BPH, as a result of studies demonstrating that this subtype predominates in the urethra and prostate of man (Price et al., *J. Urol.*, 1993, 150, 546–551; Faure et al., *Life Sci.*, 1994, 54, 1595–1605; Taniguchi et al., *Naunyn Schmiedeberg's Arch. Pharmacol.*, 1997, 355, 412–416), and appears to be the receptor mediating NE-induced smooth muscle contraction in these tissues (Forray et al., *Mol. Pharmacol.*, 1994, 45, 703–708; Hatano et al., *Br. J. Pharmacol.*, 1994; 113, 723–728; Marshall et al., *Br J. Pharmacol.*, 1995, 115, 781–786). The resulting tone is believed to contribute substantially to the total urinary outflow obstruction observed in patients with BPH (Furuya et al., *J. Urol.*, 1982, 128, 836–839), with the remaining being attributable to increased prostate mass. These observations have fueled the hypothesis that an alpha-1A subtype-selective antagonist may, via a selective and significant decrease in outlet resistance, lead to improved pharmacotherapy for BPH.

Alpha-1B adrenoceptors are present in the liver, heart and cerebral cortex and are believed to be involved in mediating vascular contractile and blood pressure responses. Alpha-1B adrenoceptors are also present in areas of the spinal cord which receive input from sympathetic neurons originating in the pontine micturition center and are presumed to be involved in the regulation of bladder function. Additionally, alpha-1B adrenoceptor antagonists are useful as analgesic/antihyperalgesic therapies for treating pain, including symptoms of acute pain, inflammatory pain, neuropathic pain (including thermal and mechanical hyperalgesia as well as thermal and mechanical allodynia), complex regional pain syndromes (including reflex sympathetic dystrophy, causalgia and sympathetically maintained pain and the like).

However, it must be noted that in BPH, it is often the irritative symptoms which prompt the patient to seek treatment, and that these irritative symptoms may be present even in patients with no demonstrable obstruction (i.e. normal urine flow rates). By combining both alpha-1A and alpha-1B subtype selectivity in a compound, a reduction of both obstructive and irritative symptoms in patients with BPH may be achieved. Lower levels or lack of alpha-1D adrenoceptor antagonism should lead to reduced or fewer side effects than those associated with the use of non-subtype-selective agents.

In a preferred embodiment, the compounds of this invention are useful for treating disorders and symptoms which can be ameliorated by blockade of alpha-1A/B adrenoceptors, such as reduction or alleviation of urinary tract disorders, for example, pelvic hypersensitivity (including interstitial cystitis, prostatitis, pelvic pain syndrome, infectious cystitis, prostatodynia, and the like), overactive bladder, urinary frequency, nocturia, urinary urgency, detrusor hyperreflexia, outlet obstruction, BPH, prostatitis, urge incontinence, urethritis, idiophatic bladder hypersensitivity, sexual dysfunction, and the like.

In another preferred embodiment, the compounds of this invention are useful for treating disorders and symptoms which can be ameliorated by blockade of alpha-1A/B adrenoceptors, such as reduction or alleviation of pain disorders, for example inflammatory pain, neuropathic pain, cancer pain, acute pain, chronic pain or complex regional pain syndromes.

In a more preferred embodiment, the compounds of this invention are useful for treating disorders and symptoms which can be ameliorated by blockade of both alpha-1A and alpha-1B adrenoceptors with diminished blockade of alpha-1D adrenoceptors, such as reduction or alleviation of both outlet obstruction, such as benign prostatic hypertrophy, and irritative symptoms associated with it, such as pain.

In another preferred embodiment, the compounds of this invention are useful for the improvement of sexual dysfunction including male erectile dysfunction (MED) and female sexual dysfunction (FSD).

These and other therapeutic uses are described, for example, in *Goodman & Gilman's, The Pharmacological Basis of Therapeutics,* ninth edition, McGraw-Hill, New York, 1996, Chapter 26, 601–616; and Coleman, R. A., *Pharmacological Reviews,* 1994, 46, 205–229.

Testing

The pharmacology of the compounds of this invention was determined by art recognized procedures. The in vitro techniques for determining the affinities of test compounds at alpha1 adrenoceptor subtypes in radioligand binding and functional assays are described in Example 20.

The effect of the compounds of this invention on blood pressure can be evaluated by any method known in the art. Examples of such methods are the Rat in Vivo Blood Pressure Assay; the Rat in Vivo Tilt-Response Assay; and the Dog in Vivo, Blood and Intraurethral Pressure assay. An in Vivo assay for measuring the blood pressure lowering effects of test compounds in normotensive rats is described in Example 21. An in Vivo assay for measuring the relative effect of a test compound on hypogastric nerve stimulation-induced increases in intraurethral pressure and phenylephrine-induced increases in diastolic blood pressure in anesthetized dogs is described in Example 24.

The analgesic activity of the compounds of this invention can be evaluated by any method known in the art. Examples of such methods are the Tail-flick Test (D'Amour et al. (1941) *J. Pharmacol. Exp. and Ther.* 72, 74–79); the Rat Tail Immersion Model, the Carrageenan-induced Paw Hyperalgesia Model, the Formalin Behavioral Response Model (Dubuisson et al., *Pain,* 1977, 4:161–174), the Von Frey Filament Test (Kim et al., *Pain,* 1992, 50,355–363), the Chronic Constriction Injury, the Radiant Heat Model, and the Cold Allodynia Model (Gogas et al., *Analgesia,* 1997, 3,111–118). An in vivo assay for measuring the effect of test compounds on the pain response to radiant heat in neuropathic rats is described in Example 22. An in vivo assay for measuring the effect of test compounds on the cold allodynia response in neuropathic rats is described in Example 23.

The potential of alpha-1 adrenoceptor antagonists to cause postural hypotension can be evaluated for example with the blood withdrawal model in the conscious rat. An in vivo assay for measuring the effect of test compounds on postural hypotension in conscious rats is described in Example 25.

Preferred compounds of this invention generally demonstrate selectivity for the alpha-1A/B subtype over the alpha-1D subtype. The compounds of this invention may reduce both obstructive and irritative symptoms in patients with BPH. The attenuated antagonism of alpha 1D-adrenoceptor is expected to lead to reduced or fewer side effects than those associated with the use of non-subtype-selective agents.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sublingual), rectal, nasal, topical, vaginal, or parenteral (including intramuscular, intraarterial, intrathecal, subcutaneous and intravenous) administration or pulmonary in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) to about 20 milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays may contain in addition to the active ingredient, such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the case of a dropper or pipette, dosing may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example on the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, and starch derivatives such as hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 13–19.

EXAMPLES

The following preparations and examples are given to enable those skilled in the art to more clearly understand and to practice the present invention. They should not be considered as limiting the scope of the invention, but merely as being illustrative and representative thereof.

Example 1

3-(6,7-Dimethoxy-3,4-dihydro-1H-isoquinolin-2-yl)-6,7-dimethoxy-2H-benzo[1,2,4]thiadiazine 1,1-dioxide

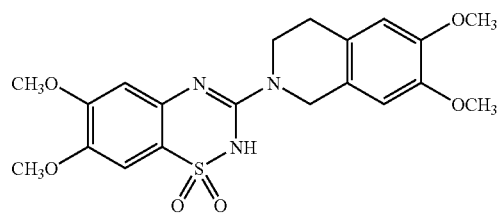

3-Chloro-6,7-dimethoxy-2H-benzo[1,2,4]thiadiazine-1,1-dioxide 1a (154 mg, 0.55 mmol) and 6,7-dimethoxy-1,2,3,4-tetrahydroisoquinoline 2a (wherein $R^1$ and $R^4$ are hydrogen, and $R^2$ and $R^3$ are methoxy) (138 mg, 0.6 mmol) were dissolved in 20 ml of methoxyethanol and heated at reflux for 72 h. The solvent was removed under reduced pressure. The gummy residue was triturated with isopropanol and the resulting crystals filtered. Recrystallization from dichloromethane afforded 120 mg of 3-(6,7-dimethoxy-3,4-dihydro-1H-isoquinolin-2-yl)-6,7-dimethoxy-2H-benzo[1,2,4]thiadiazine-1,1-dioxide 101, $[M+H]^+=434$.

Similarly the following compounds were prepared, following the procedure described above, but replacing 6,7-dimethoxy-1,2,3,4-tetrahydroisoquinoline 2a with other appropriate amines of general Formula 2:

6,7-dimethoxy-3-(4-morpholin-4-yl-5,8-dihydro-6H-pyrido[3,4d]pyrimidin-7-yl)-2H-benzo[1,2,4]thiadiazine-1,1-dioxide 102, $[M+H]^+=461$;

3-(3-cyclohexyl-5,6-dihydro-8H-imidazo[1,5-a]pyrazin-7-yl)-6,7-dimethoxy-2H-benzo[1,2,4]thiadiazine-1,1-dioxide 103, $[M+H]^+=446$, and 2-(cyclohexylamino-5,6-dihydro-8H-imidazo[1,5-a]pyrazin-7-yl)-6,7-dimethoxy-2H-benzo[1,2,4]thiadiazine-1,1-dioxide 104, $[M+H]^+=461$. Similarly, replacing 3-chloro-6,7-dimethoxy-2H-benzo[1,2,4]thiadiazine-1,1-dioxide 1a, with 2-chloro-6,7-dimethoxy-3H-quinazolin-4-one 1b, and replacing 6,7-dimethoxy-1,2,3,4-tetrahydroisoquinoline 2a with other 1,2,3,4-tetrahydroisoquinolines of general Formula 2, gave the following compounds:

2-(6,7-dimethoxy-3,4-dihydro-1H-isoquinolin-2-yl)-6,7-dimethoxy-1H-quinazolin-4-one 105, mp. 188.6–190.4° C.;

6,7-dimethoxy-2-[5-(4-methoxy-phenyl)-3,4-dihydro-1H-isoquinolin-2-yl]-3H-quinazolin-4-one 106, $[M+H]^+=443$;

2-(8-fluoro-3,4-dihydro-1H-isoquinolin-2-yl)-6,7-dimethoxy-3H-quinazolin-4-one 107, $[M+H]^+=443$;

2-(7,8-dihydro-5H-[1,3]dioxolo[4,5-g]isoquinolin-6-yl)-6,7-dimethoxy-3H-quinazolin-4-one 108, $[M+H]^+=381$;

6,7-dimethoxy-2-[7-(4-methoxy-phenyl)-3,4-dihydro-1H-isoquinolin-2-yl]-3H-quinazolin-4-one 109, $[M+H]^+=444$;

2-(5-amino-3,4-dihydro-1H-isoquinolin-2-yl)-6,7-dimethoxy-3H-quinazolin-4-one 110, $[M+H]^+=425$;

6,7-dimethoxy-2-[8-(4-methoxy-phenyl)-3,4-dihydro-1H-isoquinolin-2-yl]-3H-quinazolin-4-one 111, $[M+H]^+=443$;

6,7-dimethoxy-2-(5-pyridin-3-yl-3,4-dihydro-1H-isoquinolin-2-yl)-3H-quinazolin-4-one 112, $[M+H]^+=415$;

6,7-dimethoxy-2-(7-pyrrolidin-1-yl-3,4-dihydro-1H-isoquinolin-2-yl)-3H-quinazolin-4-one 113, [M+H]⁺=406;

6,7-dimethoxy-2-(5-pyrrolidin-1-yl-3,4-dihydro-1H-isoquinolin-2-yl)-3H-quinazolin-4-one 114, [M+H]⁺=406;

2-(5,8-dimethoxy-3,4-dihydro-1H-isoquinolin-2-yl)-6,7-dimethoxy-1H-quinazolin-4-one 115, [M+H]⁺=398;

6,7-dimethoxy-2-(5-pyridin-4-yl-3,4-dihydro-1H-isoquinolin-2-yl)-3H-quinazolin-4-one 116, [M+H]⁺=415;

6,7-dimethoxy-2-(5-pyrimidin-5-yl-3,4-dihydro-1H-isoquinolin-2-yl)-3H-quinazolin-4-one 117, [M+H]⁺=416;

2-(6,7-dimethoxy-4-oxo-3,4-dihydro-quinazolin-2-yl)-6,7-dimethoxy-1,2,3,4-tetrahydro-isoquinoline-5-carbonitrile 118, [M+H]⁺=422;

6,7-dimethoxy-2-[5-(1-pyridin-3-yl-methanoyl)-3,4-dihydro-1H-isoquinolin-2-yl]-3H-quinazolin-4-one 119, [M+H]⁺=416;

6,7-dimethoxy-2-[5-(1H-pyrrol-2-yl)-3,4-dihydro-1H-isoquinolin-2-yl]-3H-quinazolin-4-one 120, [M+H]⁺=403;

5-[2-(6,7-dimethoxy-4-oxo-3,4-dihydro-quinazolin-2-yl)-1,2,3,4-tetrahydro-isoquinolin-5-yl]-1H-pyrimidine-2,4-dione 121, [M+H]⁺=448;

2-[5-(4,5-dihydro-1H-imidazol-2-yl)-3,4-dihydro-1H-isoquinolin-2-yl]-6,7-dimethoxy-3H-quinazolin-4-one 127, [M+H]⁺=406;

2-[5-(1H-imidazol-2-yl)-3,4-dihydro-1H-isoquinolin-2-yl]-6,7-dimethoxy-3H-quinazolin-4-one 128, [M+H]⁺=404;

6,7-dimethoxy-2-[5-(1-morpholin-4-yl-methanoyl)-3,4-dihydro-1H-isoquinolin-2-yl]-3H-quinazolin-4-one 129, [M+H]⁺=451;

6,7-dimethoxy-2-[5-(pyridin-2-ylamino)-3,4-dihydro-1H-isoquinolin-2-yl]-1H-quinazolin-4-one 130, [M+H]⁺=430; and 6,7-dimethoxy-2-(5-morpholin-4-yl-3,4-dihydro-1H-isoquinolin-2-yl)-1H-quinazolin-4-one 131, [M+H]⁺=423.

Similarly, replacing 3-chloro-6,7-dimethoxy-2H-benzo[1,2,4]thiadiazine-1,1-dioxide 1a, with 2-chloro-6,7-dimethoxy-3H-quinazolin-4-one 1b, and replacing 6,7-dimethoxy-1,2,3,4-tetrahydroisoquinoline 2a with other 1,2,3,4-tetrahydroisoquinoline of general Formula 2, wherein R¹ is not hydrogen gave the following compounds:

6,7-dimethoxy-2-(6-methoxy-3-methyl-3,4-dihydro-1H-isoquinolin-2-yl)-3H-quinazolin-4-one 132, M⁺=381;

2-(1-isopropyl-3,4-dihydro-1H-isoquinolin-2-yl)-6,7-dimethoxy-3H-quinazolin-4-one 133, M⁺=355;

6,7-dimethoxy-2-(4-phenyl-3,4-dihydro-1H-isoquinolin-2-yl)-1H-quinazolin-4-one 134, [M+H]⁺=414;

2-[(3,4-dimethoxy-benzyl)-dimethylamino-3,4-dihydro-1H-isoquinolin-2-yl]-6,7-dimethoxy-1H-quinazolin-4-one 135, [M+H]⁺=531;

2-(1-benzyl-6,7-difluoro-3,4-dihydro-1H-isoquinolin-2-yl)-6,7-dimethoxy-1H-quinazolin-4-one 136, [M+H]⁺=464;

2-[2-(6,7-dimethoxy-4-oxo-1,4-dihydro-quinazolin-2-yl)-1,2,3,4-tetrahydro-isoquinolin-1-yl]-N-phenyl-acetamide 137 [M+H]⁺=471;

2-[7-chloro-6-methoxy-1-(2p-tolyl-ethyl)-3,4-dihydro-1H-isoquinolin-2-yl]-6,7-dimethoxy-1H-quinazolin-4-one 138 [M+H]⁺=521;

2-(7-chloro-6-methoxy-1p-tolyl-3,4-dihydro-1H-isoquinolin-2-yl)-6,7-dimethoxy-1H-quinazolin-4-one 139 [M+H]⁺=493;

2-[7-chloro-6-methoxy-1-(2-pyridin-4-yl-ethyl)-3,4-dihydro-1H-isoquinolin-2-yl]-6,7-dimethoxy-1H-quinazolin-4-one 140 [M+H]⁺=508;

2-(6,7-dimethoxy-3-methyl-3,4-dihydro-1H-isoquinolin-2-yl)-6,7-dimethoxy-1H-quinazolin-4-one 141 [M+H]⁺=412;

2-(6,7-dihydroxy-1-methyl-3,4-dihydro-1H-isoquinolin-2-yl)-6,7-dimethoxy-1H-quinazolin-4-one 142 [M+H]⁺=412, and 2-[5-(2-hydroxymethyl-phenyl)-3,4-dihydro-1H-isoquinolin-2-yl]-6,7-dimethoxy-3H-quinazolin-4-one 148 [M+H]⁺=444; mp=219–230° C.

Similarly, replacing 3-chloro-6,7-dimethoxy-2H-benzo[1,2,4]thiadiazine-1,1-dioxide 1a, with 2-chloro-6,7-dimethoxy-3H-quinazolin-4-one 1b, and replacing 6,7-dimethoxy-1,2,3,4-tetrahydroisoquinoline 2a with commercially available tetrahydro-β-carboline analogs of general Formula 2, gave the following compounds:

6,7-dimethoxy-2-(1,3,4,9-tetrahydro-β-carbolin-2-yl)-3H-quinazolin-4-one 143 [M+H]⁺=377;

6,7-dimethoxy-2-(6-methoxy-1,3,4,9-tetrahydro-β-carbolin-2-yl)-3H-quinazolin-4-one 144 [M+H]⁺=377; and 6,7-dimethoxy-2-(7-methylsulfanyl-1,3,4,9-tetrahydro-β-carbolin-2-yl)-3H-quinazolin-4-one 145 M⁺=422.

Similarly, replacing 3-chloro-6,7-dimethoxy-2H-benzo[1,2,4]thiadiazine-1,1-dioxide 1a, with 2-chloro-6,7-dimethoxy-3H-quinazolin-4-one 1b, and replacing 6,7-dimethoxy-1,2,3,4-tetrahydroisoquinoline 2a with naphthyridines of general Formula 2, gave the following compounds:

2-(3,4-dihydro-1H-2,7,10-triaza-anthracen-2-yl)-6,7-dimethoxy-3H-quinazolin-4-one 146 [M+H]⁺=390; and 2-(3,4-dihydro-1H-[2,7]naphthyridin-2-yl)-6,7-dimethoxy-1H-quinazolin-4-one 147 [M+H]⁺=339.

Example 2

6,7-Dimethoxy-2-(4-morpholin-4-yl-5,8-dihydro-6H-pyrido[3,4-d]pyrimidin-7-yl)-3H-quinazolin-4-one

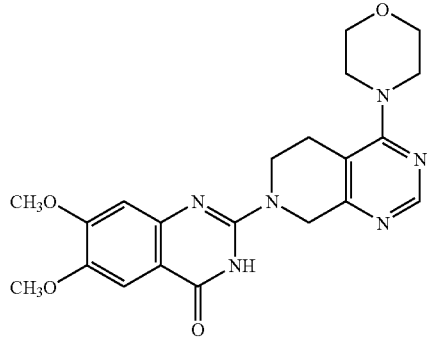

Step 1:

7-Benzyl-4-chloro-5,6,7,8-tetrahydro-pyrido[3,4-d]pyrimidine

To a mixture of 7-benzyl-5,6,7,8-tetrahydro-3H-pyrido[3,4-d]pyrimidin-4-one 3a (1.0 g, 4.14 mmol) and N,N-diethylaniline (0.37 g, 2.48 mmol) was slowly added POCl₃ (12 mL). The mixture was heated to 80° C. for 20 h. After evaporation of the excess of POCl₃, the residue was poured into ice, dichloromethane was added and the mixture was made basic (pH=11) with solid Na₂CO₃. The product was extracted with dichloromethane, dried, and concentrated. Flash column chromatography with 20% ethyl acetate:hexane gave 0.46 g of 7-benzyl-4-chloro-5,6,7,8-tetrahydro-pyrido[3,4-d]pyrimidine 4a as a yellow oil.

Step 2:

7-Benzyl-4-morpholin-4-yl-5,6,7,8-tetrahydro-pyrido[3,4-d]pyrimidine

To a solution of 7-benzyl-4-chloro-5,6,7,8-tetrahydro-pyrido[3,4-d]pyrimidine 4a (0.46 g, 1.77 mmol) in isopropanol (20 mL) was added morpholine (0.38 g, 4.42 mmol), and the reaction mixture was heated to reflux for 18 h. The solvent was removed in vacuo, and the residue was suspended in a saturated solution of NaHCO$_3$, and the product was extracted with dichloromethane. The combined organic extracts were dried over MgSO$_4$ and concentrated in vacuo to provide a residue, which was purified by chromatography to give 0.55 g of 7-benzyl-4-morpholin-4-yl-5,6,7,8-tetrahydro-pyrido[3,4-d]pyrimidine 5a as a pale yellow liquid.

Step 3:

4-Morpholin-4-yl-5,6,7,8-tetrahydro-pyrido[3,4-d]pyrimidine

7-Benzyl-4-morpholin-4-yl-5,6,7,8-tetrahydro-pyrido[3,4-d]pyrimidine 5a (0.55 g, 1.77 mmol) was dissolved in methanol (35 mL) under nitrogen. 10% Pd/C (0.55 g) was added under nitrogen followed by ammonium formate (1.12 g, 17.72 mmol) and the mixture was heated to reflux for 12 h. The catalyst was removed by filtration, washed with MeOH and the filtrate was concentrated. Flash column chromatography eluting with 5% MeOH/CH$_2$Cl$_2$ containing 0.5% of NH$_4$OH gave 0.27 g of 4-morpholin-4-yl-5,6,7,8-tetrahydro-pyrido[3,4-d]pyrimidine 6a as a pale yellow dense liquid.

Step 4:

6,7-Dimethoxy-2-(4-morpholin-4-yl-5,8-dihydro-6H-pyrido[3,4-d]pyrimidin-7-yl)-3H-quinazolin-4-one.

A mixture of 2-chloro-6,7-dimethoxy-3H-quinazolin-4-one 1b (0.28 g, 1.18 mmol) and 4-morpholin-4-yl-5,6,7,8-tetrahydro-pyrido[3,4-d]pyrimidine 6a (0.26 g, 1.20 mmol) in methoxyethanol (10 mL) was heated to 100° C. with stirring for 18 h. After cooling to room temperature, the precipitated solid was separated by filtration, washed with methoxyethanol and dried to give 0.31 g of 6,7-dimethoxy-2-(4-morpholin-4-yl-5,8-dihydro-6H-pyrido[3,4-d]pyrimidin-7-yl)-3H-quinazolin-4-one 201, mp. 287.7–290.4° C.

Similarly, following the procedure described above, but substituting 4-morpholin-4-yl-5,6,7,8-tetrahydro-pyrido[3,4-d]pyrimidine 6a in Step 4 with other appropriate substituted 5,6,7,8-tetrahydro-pyrido[3,4-d]pyrimidines of general Formula 6, the following compounds were prepared:

2-(4-benzylamino-5,8-dihydro-6H-pyrido[3,4-d]pyrimidin-7-yl)-6,7-dimethoxy-3H-quinazolin-4-one 202; [M+H]$^+$=445;

6,7-dimethoxy-2-[4-(4-methyl-piperazin-1-yl)-5,8-dihydro-6H-pyrido[3,4-d]pyrimidin-7-yl]-3H-quinazolin-4-one 203, [M+H]$^+$=438;

6,7-dimethoxy-2-{4-[4-(2-methoxy-phenyl)-piperidin-1-yl]-5,8-dihydro-6H-pyrido[3,4-d]pyrimidin-7-yl}-3H-quinazolin-4-one 204, [M+H]$^+$=529;

6,7-dimethoxy-2-{4-[(2-methoxy-ethyl)-methyl-amino]-5,8-dihydro-6H-pyrido[3,4-d-pyrimidin-7-yl}-3H-quinazolin-4-one 205, [M+H]$^+$=427;

6,7-dimethoxy-2-(4-piperidin-1-yl-5,8-dihydro-6H-pyrido[3,4-d]pyrimidin-7-yl)-3H-quinazolin-4-one 206, [M+H]$^+$=423;

2-(2-isopropyl-4-morpholin-4-yl-5,8-dihydro-6H-pyrido[3,4-d]pyrimidin-7-yl)-6,7-dimethoxy-3H-quinazolin-4-one 207, [M+H]$^+$=467;

6,7-dimethoxy-2-[4-(6-methyl-pyridin-2-ylamino)-5,8-dihydro-6H-pyrido[3,4-d]pyrimidin-7-yl]-3H-quinazolin-4-one 208, [M+H]$^+$=446;

2-{4-[(2-hydroxy-ethyl)-methyl-amino]-5,8-dihydro-6H-pyrido[3,4-d]pyrimidin-7-yl}-6,7-dimethoxy-3H-quinazolin-4-one 209, [M+H]$^+$=413;

2-[4-(4-hydroxy-piperidin-1-yl)-5,8-dihydro-6H-pyrido[3,4-d]pyrimidin-7-yl]-6,7-dimethoxy-3H-quinazolin-4-one 210, [M+H]$^+$=439;

6,7-dimethoxy-2-[4-((S)-2-methoxymethyl-pyrrolidin-1-yl)-5,8-dihydro-6H-pyrido[3,4-d]pyrimidin-7-yl]-3H-quinazolin-4-one 211, [M+H]$^+$=453;

2-[4-(2,6-dimethyl-morpholin-4-yl)-5,8-dihydro-6H-pyrido[3,4-d]pyrimidin-7-yl]-6,7-dimethoxy-3H-quinazolin-4-one 212, [M+H]$^+$=453;

2-[4-(hexyl-methyl-amino)-5,8-dihydro-6H-pyrido[3,4-d]pyrimidin-7-yl]-6,7-dimethoxy-3H-quinazolin-4-one 213, [M+H]$^+$=453; and 6,7-dimethoxy-2-(4-pyrrolidin-1-yl-5,8-dihydro-6H-pyrido[3,4d]pyrimidin-7-yl)-3H-quinazolin-4-one 214, [M+H]$^+$=409.

Example 3

2-(3-Cyclohexylamino-5,6-dihydro-8H-imidazo[1,5-a]pyrazin-7-yl)-6,7-dimethoxy-3H-quinazolin-4-one

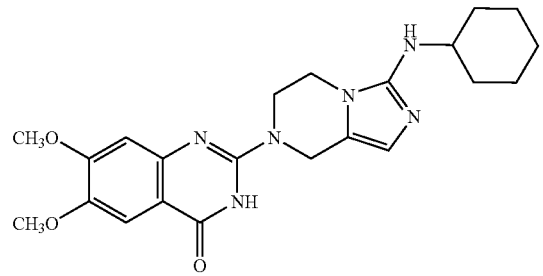

Step 1:

3-Cyclohexyl-5,6,7,8-tetrahydro-imidazo[1,5-a]pyrazine

A solution of 3-cyclohexyl-imidazo[1,5-a]pyrazine 8a (960 mg, 4.4 mmol) in 25 ml ethanol was treated with 100 mg Adam's catalyst and stirred vigorously under one atmosphere of hydrogen for 18 hr. The mixture was filtered through a pad of Celite®. The filtrate was concentrated in vacuo to yield 790 mg of 3-cyclohexyl-5,6,7,8-tetrahydro-imidazo[1,5-a]pyrazine 9a as a greenish-yellow solid.

Step 2:

2-(3-Cyclohexylamino-5,6-dihydro-8H-imidazo[1,5-a]pyrazin-7-yl)-6,7-dimethoxy-1H-quinazolin-4-one 3-Cyclohexyl-5,6,7,8-tetrahydro-imidazo[1,5-a]pyrazine 9a (363 mg, 1.6 mmol) and 2-chloro-6,7-dimethoxy-1H-quinazolin-4-one 1b (384 mg, 1.6 mmol) were suspended in 20 ml methoxyethanol, purged briefly with nitrogen, and heated at 100° C. for 10 h. The solvent was removed by distillation and the residue was purified by flash chromatography to give a pale yellow solid which was slurried with hot ethanol and allowed to cool to ambient temperature.

Vacuum filtration provided 274 mg of 2-(3-cyclohexylamino-5,6-dihydro-8H-imidazo[1,5-a]pyrazin-7-yl)-6,7-dimethoxy-1H-quinazolin-4-one 301, [M+H]$^+$=425, as a white solid.

The hydrochloride salt was prepared by stirring a suspension of 2-(3-cyclohexylamino-5,6-dihydro-8H-imidazo[1,5-a]pyrazin-7-yl)-6,7-dimethoxy-1H-quinazolin-4-one (50 mg, 0.12 mmol) in 4 ml methanol and acidifying with 1 N hydrochloric acid (0.12 ml, 0.12 mmol), diluting the resulting solution with ethanol and allowing to stand overnight. The yellow needles of the hydrochloride salt (32 mg) were collected by vacuum filtration and oven dried at 50° C.

Similarly, following the procedure described above, but substituting 3-cyclohexyl-imidazo[1,5-a]pyrazine 8a in Step 1 with other appropriate pyrazine derivatives of general Formula 8, the following compounds were prepared:

6,7-dimethoxy-2-(3-phenyl-5,6-dihydro-8H-imidazo[1,5-a]pyrazin-7-yl)-1H-quinazolin-4-one 302 [M+H]$^+$=404;

2-(3-cyclohexyl-5,6-dihydro-8H-imidazo[1,5-a]pyrazin-7-yl)-6,7-dimethoxy-1H-quinazolin-4-one 303, [M+H]$^+$=410;

2-[3-(2,2-dimethyl-propyl)-5,6-dihydro-8H-imidazo[1,5-α]pyrazin-7-yl]-6,7-dimethoxy-1H-quinazolin-4-one 304, mp. 282–283° C., M$^+$=397;

2-(3-azepan-1-yl-5,6-dihydro-8H-imidazo[1,5-α]pyrazin-7-yl)-6,7-dimethoxy-1H-quinazolin-4-one 305, mp. 258–261.5° C., M$^+$=424;

2-(3-butyl-5,6-dihydro-8H-imidazo[1,5-α]pyrazin-7-yl)-6,7-dimethoxy-1H-quinazolin-4-one 306, mp. 248.0–249.4° C., M$^+$=383;

6,7-dimethoxy-2-(3-morpholin-4-yl-5,6-dihydro-8H-imidazo[1,5-α]pyrazin-7-yl)-1H-quinazolin-4-one 307, M$^+$=412;

6,7-dimethoxy-2-(3-piperidin-1-yl-5,6-dihydro-8H-imidazo[1,5-α]pyrazin-7-yl)-1H-quinazolin-4-one 308, M$^+$=410;

2-(3-benzylamino-5,6-dihydro-8H-imidazo[1,5-a]pyrazin-7-yl)-6,7-dimethoxy-1H-quinazolin-4-one, 309, mp. 158–163° C., M$^+$=432; and 2-(3-tert-butyl-5,6-dihydro-8H-imidazo[1,5-a]pyrazin-7-yl)-6,7-dimethoxy-1H-quinazolin-4-one, 310, [M+H]$^+$=384.

Example 4

6,7-Dimethoxy-2-[5-(4-methyl-piperazine-1-sulfonyl)-3,4-dihydro-1H-isoquinolin-2-yl]-3H-quinazolin-4-one

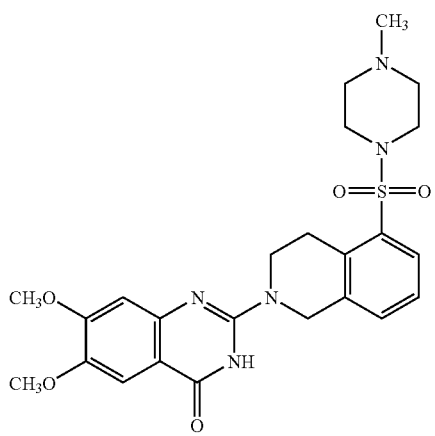

Step 1:

5-(4-Methyl-piperazine-1-sulfonyl)-1,2,3,4-tetrahydro-isoquinoline 5-(4-Methyl-piperazine-1-sulfonyl)-isoquinoline 10a (0.99 g, 3.41 mmol) was dissolved in a solution 2% of HCl in methanol (100 mL) under nitrogen. PtO$_2$ (250 mg) was added under nitrogen and the mixture was hydrogenated in a Parr apparatus at 45 psi for 3.5 h. The catalyst was removed by filtration, rinsed with MeOH, and the filtrate was concentrated in vacuo to give 1.25 g of 5-(4-methyl-piperazine-1-sulfonyl)-1,2,3,4-tetrahydro-isoquinoline 11a as a pale yellow foam. The crude hydrochloride salt of the product was used in the next step without further purification.

Step 2:

6,7-Dimethoxy-2-[5-(4-methyl-piperazine-1-sulfonyl)-3,4-dihydro-1H-isoquinolin-2-yl]-3H-quinazolin-4-one A mixture of 2-chloro-6,7-dimethoxy-3H-quinazolin-4-one 1b, (0.77 g, 3.23 mmol), 5-(4-methyl-piperazine-1-sulfonyl)-1,2,3,4-tetrahydro-isoquinoline 11a (1.25 g, 3.41 mmol) and triethylamine (0.75 g, 1.04 mL, 7.46 mmol) in DMSO (15 mL) was heated at 80° C. with stirring for 18 h. After cooling to room temperature the reaction was diluted with water. The precipitated white product was collected by filtration, washed with water, and dried to give 0.6 g of 6,7-dimethoxy-2-[5-(4-methyl-piperazine-1-sulfonyl)-3,4-dihydro-1H-isoquinolin-2-yl]-3H-quinazolin-4-one 401, mp. 230–237° C.

Similarly other compounds were prepared substituting 5-(4-methyl-piperazine-1-sulfonyl)-isoquinoline of general Formula 10a, with other isoquinolines of general Formula 10.

5-(morpholine-4-sulfonyl)-isoquinoline gave 6,7-dimethoxy-2-[5-(morpholine-4-sulfonyl)-3,4-dihydro-1H-isoquinolin-2-yl]-3H-quinazolin-4-one 402 [M+H]$^+$=487;

1,2,3,4-tetrahydro-isoquinoline-7-sulfonic acid (2-pyridin-2-yl-ethyl)-amide gave 2-(6,7-dimethoxy-4-oxo-1,4-dihydro-quinazolin-2-yl)-1,2,3,4-tetrahydro-isoquinoline-7-sulfonic acid (2-pyridin-2-yl-ethyl)-amide 403, [M+H]$^+$=522.6; and 7-(morpholine-4-sulfonyl)-3,4-dihydro-1H-isoquinoline gave 6,7-dimethoxy-2-[7-(morpholine-4-sulfonyl)-3,4-dihydro-1H-isoquinolin-2-yl]-3H-quinazolin-4-one 404, [M+H]$^+$=487.

Example 5

2-(1-Benzyl-1,4,6,7-tetrahydro-imidazo[4,5-c]pyridin-5-yl)-6,7-dimethoxy-3H-quinazolin-4-one

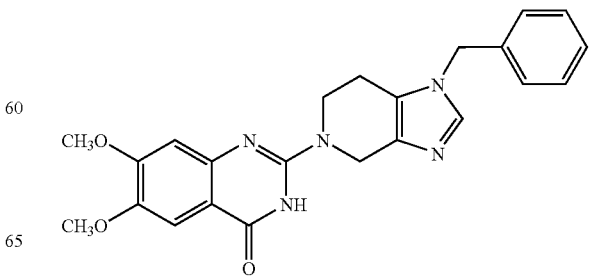

Step 1:

1-(tert-Butoxycarbonyl)-4-(2-(tert-butoxycarbonylamino)ethylimidazole 13

Di-tert-butyl dicarbonate (65.0 g, 0.298 mol) was added in small portions to a solution of histamine dihydrochloride 12 (25.0 g, 0.136 mol) and triethylamine (42 ml, 0.298 mol) in MeOH at 0° C. The resulting mixture was warmed to room temperature and stirred for 12 hours, then diluted with ethyl acetate (500 ml), and washed with saturated sodium bicarbonate (200 ml). The organic phase was dried over magnesium sulfate and concentrated in vacuo to give 1-(tert-butoxycarbonyl)4-(2-(tert-butoxycarbonylamino) ethyl imidazole 13 as a white solid (22.6 g).

Step 2:

1-Benzyl-5-(2-(tert-butoxycarbonylamino)ethyl imidazole 14

Benzyl alcohol (3.7 ml, 35 mmol) and diisopropylethylamine (6.2 ml, 25 mmol) in dichloromethane (50 mL) was added dropwise to a solution of triflic anhydride (10.0 g, 35 mmol) in anhydrous dichloromethane (50 mL) at −78° C. over a period of 20 min. The resulting mixture was stirred at −78° C. for an additional 30 min, then was added dropwise 1-(tert-butoxycarbonyl)-4-(2-(tert-butoxycarbonylamino) ethylimidazole 13 (10.0 g, 35 mmol) in dichloromethane (50 mL). The reaction mixture was stirred at −78° C. for 30 min, and then gradually warmed to room temperature. After 12 hours, the reaction mixture was poured into phosphate buffer (pH=7, 300 mL), stirred for 30 min, and extracted with ethyl acetate (2×300 mL). The combined organic layers were dried over magnesium sulfate and concentrated in vacuo to provide a light brown oil, which was purified by column chromatography to give 1-benzyl-5-(2-(tert-butoxycarbonylamino)ethylimidazole 14 as an colorless oil (8.1 g).

Step 3:

1-Benzyl-1,4,6,7-tetrahydro-imidazo[4,5-c]pyridine

1-Benzyl-5-(2-(tert-butoxycarbonylamino)ethylimidazole 14 (6.5 g, 21.6 mmol) was dissolved in 50% trifluoroacetic acid/dichloromethane and stirred at 0° C. for 30 min. The reaction mixture was concentrated in vacuo to give 1-benzyl-5-aminoethyl-imidazole trifluoroacetic acid salt a colorless oil, which was dissolved in 1 N hydrochloric acid (100 mL) and added aqueous formaldehyde (5.3 g, 64.8 mmol). The resulting reaction mixture was heated to reflux for 1.5 hours, concentrated in vacuo and crystallized by trituration with isopropanol to yield 1-benzyl-1,4,6,7-tetrahydro-imidazo[4,5-c]pyridine 15a as the dihydrochloride salt (4.6 g).

Step 4:

2-(1-Benzyl-1,4,6,7-tetrahydro-imidazo[4,5-c]pyridin-5-yl)-6,7-dimethoxy-1H-quinazolin-4-one A mixture of 2-chloro-6,7-dimethoxy-3H-quinazolin-4-one 1 (wherein R is methyl and Z is —C(O)—, 296 mg, 1.24 mmol), 1-benzyl-1,4,6,7-tetrahydro-imidazo[4,5-c]pyridine dihydrochloride 15a (440 mg, 1.54 mmol)) and diisopropylethylamine (1.2 g, 9.26 mmol) in 2-methoxyethanol (10 mL) was stirred at 120° C. for 6 hours. The reaction mixture was concentrated in vacuo to give an oil residue, which was diluted with water. The white precipitate that formed was collected by filtration to give 155 mg of 2-(1-benzyl-1,4,6,7-tetrahydro-imidazo[4,5-c]pyridin-5-yl)-6,7-dimethoxy-3H-quinazolin-4-one 501, [M+H]$^+$=418.

Example 6

6,7-Dimethoxy-2-(1-m-tolyl-1,4,6,7-tetrahydro-imidazo[4.5-c]pyridin-5-yl)-1H-quinazolin-4-one

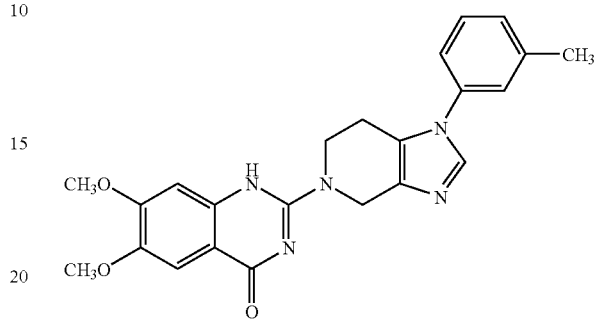

Step 1:

5-Benzyl-1-m-tolyl-4,5,6,7-tetrahydro-1H-imidazo[4,5-c]pyridine

A solution of 1-benzyl-4,4-diethoxy-piperidin-3-ylamine 16 (600 mg, 2.2 mmol), and m-tolyl isothiocyanate (328 mg, 2.2 mmol) in 10 mL chloroform was heated at 60° C. for 2 hr. The solvent was removed in vacuo, and the residue was treated with 10 mL each of 10% hydrochloric acid and dioxane and heated at reflux for 1 h. After removal of the solvent the residue was dissolved in 50 mL ethanol followed by addition of Raney Nickel (ca. 3.0 g). The suspension was heated at reflux for 2 h then allowed to cool to room temperature. The solids were removed by filtration. The solvent was evaporated in vacuo, and the residue was diluted with 10% sodium hydroxide solution and extracted into chloroform. The organic layer was dried over potassium carbonate, filtered and concentrated to provide 500 mg of 5-benzyl-1-m-tolyl-4,5,6,7-tetrahydro-1H-imidazo[4,5-c]pyridine 17a as a light brown oil, [M+H]$^+$=304.

Step 2:

1-m-Tolyl-4,5,6,7-tetrahydro-1H-imidazo[4,5-c]pyridine

A mixture of 5-benzyl-1-m-tolyl-4,5,6,7-tetrahydro-1H-imidazo[4,5-c]pyridine 17a (500 mg, 1.6 mmol), ammonium formate (1.0 g), and 700 mg 5% Pd/C (50% with water) in 80% aqueous methanol was heated at reflux for 12 hr, and then allowed to reach ambient temperature. The catalyst was removed by filtration through Celite®. The filtrate was evaporated in vacuo. Purification by silica gel chromatography provided 1-m-tolyl-4,5,6,7-tetrahydro-1H-imidazo[4,5-c]pyridine (110 mg) 18a as an oil.

Step 3:

6,7-Dimethoxy-2-(1-m-tolyl-1,4,6,7-tetrahydro-imidazo[4,5-c]pyridin-5-yl)-1H-quinazolin-4-one A mixture of 1-m-tolyl-4,5,6,7-tetrahydro-1H-imidazo[4,5-c]pyridine 18a (100 mg, 0.5 mmol), 2-chloro-6,7-dimethoxy-3H-quinazolin-4-one 1b (100 mg, 0.4 mmol), and triethylamine (140 μL, 1.0 mmol) in 10 mL methoxyethanol was heated at 100° C. under nitrogen for 12 hr. The mixture was pumped to constant weight. The resulting residue was slurried with hot ethanol and allowed to reach ambient temperature. Vacuum filtration provided 95 mg of 6,7-dimethoxy-2-(1-m-tolyl-1,4,6,7-tetrahydro-imidazo[4,5-c]pyridin-5-yl)-3H-quinazolin-4-one, 601, [M+H]⁺=418, as a white solid.

Similarly following the procedure described above, the following compounds of Formula I can be prepared:

6,7-dimethoxy-2-(1-phenyl-1,4,6,7-tetrahydro-imidazo[4,5-c]pyridin-5-yl)-3H-quinazolin-4-one 602, [M+H]⁺=404;

6,7-dimethoxy-2-(3-phenyl-3,4,6,7-tetrahydro-imidazo[4,5-c]pyridin-5-yl)-3H-quinazolin-4-one, 603, [M+H]⁺=404;

6,7-dimethoxy-2-(1,4,6,7-tetrahydro-imidazo[4,5-c]pyridin-5-yl)-3H-quinazolin-4-one, 604, [M+H]⁺=328.4;

6,7-dimethoxy-2-[2-(1-phenyl-methanoyl)-1,4,5,7-tetrahydro-pyrrolo[2,3-c]pyridin-6-yl]-3H-quinazolin-4-one, 605, [M+H]⁺=413;

2-[1-(4-chloro-phenyl)-1,4,6,7-tetrahydro-imidazo[4,5-c]pyridin-5-yl]-6,7-dimethoxy-3H-quinazolin-4-one, 606, [M+H]⁺=438;

6,7-dimethoxy-2-(1-naphthalen-2-yl-1,4,6,7-tetrahydro-imidazo[4,5-c]pyridin-5-yl)-3H-quinazolin-4-one, 607, [M+H]⁺=454;

6,7-dimethoxy-2-[1-(4-methoxy-phenyl)-1,4,6,7-tetrahydro-imidazo[4,5-c]pyridin-5-yl]-3H-quinazolin-4-one, 608, [M+H]⁺=434;

2-[1-(2-chloro-phenyl)-1,4,6,7-tetrahydro-imidazo[4,5-c]pyridin-5-yl]-6,7-dimethoxy-3H-quinazolin-4-one, 609, [M+H]⁺=438;

2-[1-(3-chloro-phenyl)-1,4,6,7-tetrahydro-imidazo[4,5-c]pyridin-5-yl]-6,7-dimethoxy-3H-quinazolin-4-one, 610, [M+H]⁺=438;

6,7-dimethoxy-2-[1-(3-trifluoromethyl-phenyl)-1,4,6,7-tetrahydro-imidazo[4,5c]pyridin-5-yl]-3H-quinazolin-4-one, 611, [M+H]⁺=472;

2-(1-benzo[1,3]dioxol-5-yl-1,4,6,7-tetrahydro-imidazo[4,5-c]pyridin-5-yl)-6,7-dimethoxy-3H-quinazolin-4-one, 612, [M+H]⁺=448;

2-(1-isobutyl-1,4,6,7-tetrahydro-imidazo[4,5-c]pyridin-5-yl)-6,7-dimethoxy-1H-quinazolin-4-one, 613, [M+H]⁺=384;

6,7-dimethoxy-2-[1-(3-methoxy-propyl)-1,4,6,7-tetrahydro-imidazo[4,5-c]pyridin-5-yl]-1H-quinazolin-4-one, 614, [M+H]⁺=400;

2-(1-cycloheptyl-1,4,6,7-tetrahydro-imidazo[4,5-c]pyridin-5-yl)-6,7-dimethoxy-1H-quinazolin-4-one, 615, [M+H]⁺=424;

2-(1-sec-butyl-1,4,6,7-tetrahydro-imidazo[4,5-c]pyridin-5-yl)-6,7-dimethoxy-1H-quinazolin-4-one, 616, [M+H]⁺=384;

6,7-dimethoxy-2-[1-(1-methyl-butyl)-1,4,6,7-tetrahydro-imidazo[4,5-d]pyridin-5-yl]-1H-quinazolin-4-one, 617, [M+H]⁺=398;

6,7-dimethoxy-2-[1-(2-methyl-butyl)-1,4,6,7-tetrahydro-imidazo[4,5-d]pyridin-5-yl]-1H-quinazolin-4-one, 618, [M+H]⁺=398;

2-(1-cyclohexyl-1,4,6,7-tetrahydro-imidazo[4,5-c]pyridin-5-yl)-6,7-dimethoxy-1H-quinazolin-4-one, 619, [M+H]⁺=410;

6,7-dimethoxy-2-[1-(tetrahydro-furan-2-ylmethyl)-1,4,6,7-tetrahydro-imidazo[4,5-c]pyridin-5-yl]-1H-quinazolin-4-one, 620, [M+H]⁺=412; and 2-(1-cyclopentyl-1,4,6,7-tetrahydro-imidazo[4,5-c]pyridin-5-yl)-6,7-dimethoxy-1H-quinazolin-4-one, 621, [M+H]⁺=396.

Example 7

6,7-Dimethoxy-2-(5-morpholin-4-ylmethyl-3,4-dihydro-1H-isoquinolin-2-yl)-3H-quinazolin-4-one

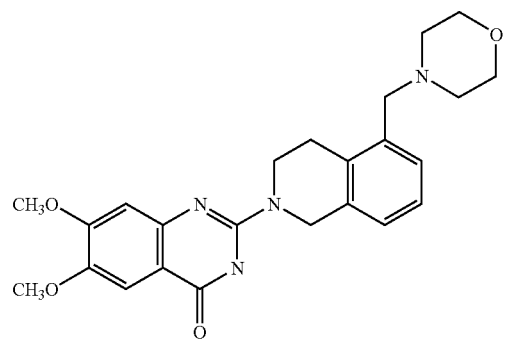

Step 1:

5-Formyl-3,4-dihydro-1H-isoquinoline-2-carboxylic acid tert-butyl ester

A solution of 5-bromo-3,4-dihydro-1H-isoquinoline-2-carboxylic acid tert-butyl ester 19a (3.87 g, 12.39 mmol) in diethyl ether (60 mL) was cooled to −100° C. A solution of 1.7 M tert-butyllithium in hexanes (16.04 mL, 27.27 mmol) was added dropwise. After the addition, stirring was continued for 30 min to −100° C. 4-Formylmorpholine (1.87 mL, 18.59 mmol) in diethyl ether (10 mL) was added all at once and the reaction was stirred for an additional 1 h. The mixture was then allowed to reach room temperature. Ammonium chloride saturated solution was added and the product was extracted with dichloromethane (3×70 mL). The combined organics were dried with magnesium sulfate, the solvent was evaporated and the residue was purified by flash chromatography eluting with 20% ethyl acetate in hexanes, to yield 0.44 g of 5-formyl-3,4-dihydro-1H-isoquinoline-2-carboxylic acid tert-butyl ester 20a.

Step 2:

5-Hydroxymethyl-3,4-dihydro-1H-isoquinoline-2-carboxVlic acid tert-butyl ester

To solution of 5-formyl-3,4-dihydro-1H-isoquinoline-2-carboxylic acid tert-butyl ester 20a (0.44 g, 1.71 mmol) in 40 mL of methanol:tetrahydrofuran (1:1) at room temperature was added sodium borohydride (0.072 g, 1.88 mmol), and the mixture was stirred to room temperature for 3 h. Water (30 mL) was added followed by ammonium chloride saturated solution (20 mL) and the product was extracted with dichloromethane. The combined organics were dried over magnesium sulfate, the solvent was evaporated and the residue was purified by flash chromatography eluting with 30% ethyl acetate in hexanes, to yield 0.31 g of 5-hydroxymethyl-3,4-dihydro-1H-isoquinoline-2-carboxylic acid tert-butyl ester 21a.

Step 3:

2-(5-Hydroxymethyl-3,4-dihydro-1H-isoquinolin-2-yl)-6,7-dimethoxy-3H-quinazolin-4-one 5-Hydroxymethyl-3,4-dihydro-1H-isoquinoline-2-carboxylic acid tert-butyl ester 21a (0.31 g, 1.17 mmol) was dissolved at room temperature in 10 mL of 10% trifluoro-acetic acid in dichloromethane and stirred for 2 h. The volatiles were evaporated, the residue was suspended in toluene, evaporated again and dried under vacuum. The trifluoroacetic salt of the deprotected amine, was mixed with 2-chloro-6,7-dimethoxy-3H-quinazolin-4-one 1b (0.269 g, 1.11 mmol) and sodium bicarbonate (0.148 g, 1.76 mmol) in dimethyl sulfoxide (6 mL), and the mixture was heated to 85° C. with stirring for 28 h. After cooling to room temperature, water (20 mL) was added and the precipitated product was separated by filtration, rinsed with water, and dried to yield 0.2 g of 2-(5-hydroxymethyl-3,4-dihydro-1H-isoquinolin-2-yl)-6,7-dimethoxy-3H-quinazolin-4-one 22a, mp. 200.1–206.3° C.

Step 4:

2-(5-Bromomethyl-3,4-dihydro-1H-isoquinolin-2-yl)-6,7-dimethoxy-3H-quinazolin-4-one 2-(5-Hydroxymethyl-3,4-dihydro-1H-isoquinolin-2-yl)-6,7-dimethoxy-1H-quinazolin-4-one 22a (0.2 g, 0.54 mmol) was dissolved to room temperature in 5 mL of 48% hydrobromic acid and stirred to room temperature for 24 h. The precipitated product was separated by filtration, rinsed with water, dried to yield 0.21 g (91%) 2-(5-bromomethyl-3,4-dihydro-1H-isoquinolin-2-yl)-6,7-dimethoxy-3H-quinazolin-4-one 23a.

Step 5

6,7-Dimethoxy-2-(5-morpholin-4-ylmethyl-3,4-dihydro-1H-isoquinolin-2-yl)-3H-quinazolin-4-one A mixture of 2-(5-bromomethyl-3,4-dihydro-1H-isoquinolin-2-yl)-6,7-dimethoxy-3H-quinazolin-4-one 23a (54 mg, 0.12 mmol), morpholine (12 mg, 0.13 mmol) and sodium bicarbonate (16 mg, 0.18 mmol) in dimethyl sulfoxide (0.5 mL) was heated to 80° C. with stirring for 18 h. After cooling to room temperature, water (2 mL) was added and the precipitated product was separated by filtration, rinsed with water and dried. 6,7-Dimethoxy-2-(5-morpholin-4-ylmethyl-3,4-dihydro-1H-isoquinolin-2-yl)-3H-quinazolin-4-one 701 was purified by flash chromatography eluting with 2% methanol in dichloromethane containing 0.2% of ammonium hydroxide. The product was converted to the hydrochloric acid salt. Yield 15 mg, mp. 227.9–229.6° C., [M+H]$^+$=437.

Similarly following the above mentioned steps, but substituting in Step 5 morpholine for the appropriate cyclic amines the following compounds were prepared:

2-[5-((S)-2-hydroxymethyl-pyrrolidin-1-ylmethyl)-3,4-dihydro-1H-isoquinolin-2-yl]-6,7-dimethoxy-3H-quinazolin-4-one 702; compound with trifluoro-acetic acid, [M+H]$^+$=451;

6,7-dimethoxy-2-[5-(4-methyl-piperazin-1-ylmethyl)-3,4-dihydro-1H-isoquinolin-2-yl]-3H-quinazolin-4-one 703; compound with trifluoro-acetic acid, [M+H]$^+$=450;

2-[5-(4-hydroxymethyl-piperidin-1-ylmethyl)-3,4-dihydro-1H-isoquinolin-2-yl]-6,7-dimethoxy-3H-quinazolin-4-one 704; compound with trifluoro-acetic acid, [M+H]$^+$=465;

6,7-dimethoxy-2-(5-piperidin-1-ylmethyl-3,4-dihydro-1H-isoquinolin-2-yl)-3H-quinazolin-4-one 705; compound with trifluoro-acetic acid, [M+H]$^+$=435; and 2-[5-(4-Hydroxy-piperidin-1-ylmethyl)-3,4-dihydro-1H-isoquinolin-2-yl]-6,7-dimethoxy-3H-quinazolin-4-one 706; compound with trifluoro-acetic acid, [M+H]+=451;

Similarly, substituting in Step 5 morpholine with sodium cyanide the following compound was prepared:

[2-(6,7-dimethoxy-4-oxo-3,4-dihydro-quinazolin-2-yl)-1,2,3,4-tetrahydro-isoquinolin-5-yl]-acetonitrile 707, [M+H]$^+$=377.

Example 8

N-[2-(6,7-Dimethoxy-4-oxo-3,4-dihydro-quinazolin-2-yl)-1,2,3,4-tetrahydro-isoquinolin-5-yl]-N,N-dimethyl-formamidine

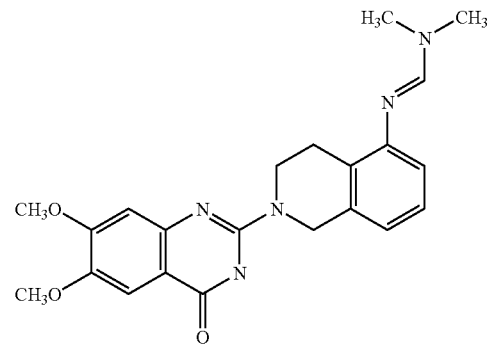

Step 1:

2-(5-Amino-3,4-dihydro-1H-isoquinolin-2-yl)-6,7-dimethoxy-3H-quinazolin-4-one

A mixture of 1,2,3,4-tetrahydro-isoquinolin-5-ylamine 24a (3.83 g, 25.84 mmol) and 2-chloro-6,7-dimethoxy-3H-quinazolin-4-one 1b (5.9 g, 24.54 mmol) in methoxyethanol (60 mL) was heated to 60° C. with stirring for 48 h. The volatiles were evaporated and the residue was purified by flash column chromatography eluting with 3% methanol in dichloromethane containing 0.3% of ammonium hydroxide to yield 4.3 g of 2-(5-amino-3,4-dihydro-1H-isoquinolin-2-yl)-6,7-dimethoxy-3H-quinazolin-4-one 110.

Step 2:

N-[2-(6,7-Dimethoxy-4-oxo-3,4-dihydro-quinazolin-2-yl)-1,2,3,4-tetrahydro-isoquinolin-5-yl]-N,N-dimethyl-formamidine To N,N-dimethylformamide (0.5 mL) was added phosphorus oxychloride (7.6 mg, 0.05 mmol) at room temperature with stirring and allowed to react for 1 h. 2-(5-Amino-3,4-dihydro-1H-isoquinolin-2-yl)-6,7-dimethoxy-1H-quinazolin-4-one 110 (18 mg, 0.05 mmol) was added all at once and stirring was continued for 24 h. The volatiles were evaporated and the residue was purified by preparative HPLC to afford the corresponding trifluoroacetic acid salt of N-[2-(6,7-dimethoxy-4-oxo-3,4-dihydro-quinazolin-2-yl)-1,2,3,4-tetrahydro-isoquinolin-5-yl]-N,N-dimethyl-formamidine 801, [M+H]$^+$=408.

In a similar fashion, the following compounds were made by substituting in Step 2 N,N-dimethylformamide with the appropriate amides:

N-[2-(6,7-dimethoxy-4-oxo-3,4-dihydro-quinazolin-2-yl)-1,2,3,4-tetrahydro-isoquinolin-5-yl]4-methoxy-benzamidine 802, [M+H]$^+$=486;

N-[2-(6,7-dimethoxy-4-oxo-3,4-dihydro-quinazolin-2-yl)-1,2,3,4-tetrahydro-isoquinolin-5-yl]-cyclopentanecarboxamidine 803, [M+H]$^+$=448;

2-[5-(4,5-dihydro-1H-imidazol-2-ylamino)-3,4-dihydro-1H-isoquinolin-2-yl]-6,7-dimethoxy-3H-quinazolin-4-one 804, [M+H]$^+$=421;

N-[2-(6,7-dimethoxy-4-oxo-3,4-dihydro-quinazolin-2-yl)-1,2,3,4-tetrahydro-isoquinolin-5-yl]-isonicotinamidine 805, [M+H]$^+$=457;

N-[2-(6,7-dimethoxy-4-oxo-3,4-dihydro-quinazolin-2-yl)-1,2,3,4-tetrahydro-isoquinolin-5-yl]-furan-2-carboxamidine 806, [M+H]$^+$=446;

N-[2-(6,7-dimethoxy-4-oxo-3,4-dihydro-quinazolin-2-yl)-1,2,3,4-tetrahydro-isoquinolin-5-yl]-cyclobutanecarboxamidine 807, [M+H]$^+$=434;

N-[2-(6,7-dimethoxy-4-oxo-3,4-dihydro-quinazolin-2-yl)-1,2,3,4-tetrahydro-isoquinolin-5-yl]-butyramidine 808, [M+H]$^+$=422;

6,7-dimethoxy-2-[5-(1-methyl-4,5-dihydro-3H-pyrrol-2-ylamino)-3,4-dihydro-1H-isoquinolin-2-yl]-3H-quinazolin-4-one 809, [M+H]$^+$=434;

2-[5-(4,5-dihydro-3H-pyrrol-2-ylamino)-3,4-dihydro-1H-isoquinolin-2-yl]-6,7-dimethoxy-3H-quinazolin-4-one 810, [M+H]$^+$=420;

6,7-dimethoxy-2-{5-[piperidin-(2E)-ylideneamino]-3,4-dihydro-1H-isoquinolin-2-yl}-3H-quinazolin-4-one 811, [M+H]$^+$=434;

3-{2-[2-(6,7-dimethoxy-4-oxo-3,4-dihydro-quinazolin-2-yl)-1,2,3,4-tetrahydro-isoquinolin-5-ylimino]-pyrrolidin-1-yl}-propionitrile 812, [M+H]$^+$=473; and 2-[5-(5,6-dihydro-2H-[1,4]thiazin-3-ylamino)-3,4-dihydro-1H-isoquinolin-2-yl]-6,7-dimethoxy-3H-quinazolin-4-one 813, [M+H]$^+$=452.

Example 9

2-[5-(Imino-morpholin-4-yl-methyl)-3,4-dihydro-1H-isoquinolin-2-yl]-6,7-dimethoxy-3H-quinazolin-4-one

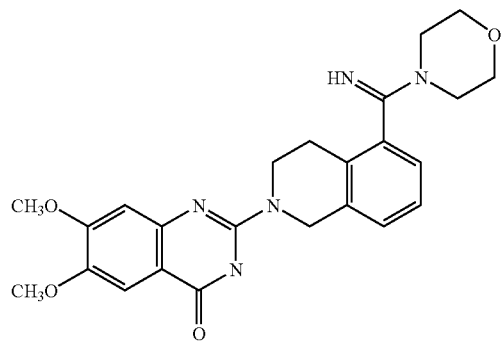

Step 1:

5-Bromo-3,4-dihydro-1H-isoquinoline-2-carboxylic acid tert-butyl ester

A mixture of 5-bromo-1,2,3,4-tetrahydro-isoquinoline 25a (5.86 g, 27.62 mmol) and di-tert-butyl dicarbonate (6.63 g, 30.39 mmol) was dissolved in THF (80 mL). Following 72 h of stirring at room temperature, the mixture was then concentrated and the residue purified by flash chromatography eluting with 3% methanol in dichloromethane containing 0.3% of ammonium hydroxide to yield 6.54 g 5-bromo-3,4-dihydro-1H-isoquinoline-2-carboxylic acid tert-butyl ester 26a, mp. 75.6–80.4° C.

Step 2:

5-(Imino-morpholin-4-yl-methyl)-3,4-dihydro-1H-isoquinoline-2-carboxylic acid tert-butyl ester A solution of 5-bromo-3,4-dihydro-1H-isoquinoline-2-carboxylic acid tert-butyl ester 26a (0.4 g, 1.28 mmol) in tetrahydrofuran (10 mL) under argon, was cooled to −78° C. A solution of 2.5 M n-butyllithium in hexanes (0.61 mL, 1.53 mmol) was added dropwise over 5 min. After the addition, stirring was continued for 15 min at −78° C. 4-Morpholinecarbonitrile (0.172 g, 1.53 mmol) was added all at once and reaction continued for 90 min at that temperature. A saturated ammonium chloride solution was added at −78° C. After warming to room temperature the mixture was made basic (pH 9) with concentrated ammonium hydroxide and the product was extracted with dichloromethane. The combined organics were dried with magnesium sulfate, the solvent was evaporated and the residue purified by flash chromatography eluting with 6% methanol in dichloromethane containing 0.6% of ammonium hydroxide, to yield 0.24 g of 5-(imino-morpholin-4-yl-methyl)-3,4-dihydro-1H-isoquinoline-2-carboxylic acid tert-butyl ester 27a.

Step 3:

5-(Imino-morpholin-4-yl-methyl)-3,4-dihydro-1H-isoquinoline 5-(Imino-morpholin-4-yl-methyl)-3,4-dihydro-1H-isoquinoline-2-carboxylic acid tert-butyl ester 27a (0.24 g, 0.69 mmol) was dissolved to room temperature in 10 mL of 10% trifluoroacetic acid in dichloromethane and stirred to room temperature for 18 h. The volatiles were evaporated, the residue was suspended in toluene and evaporated again. The residue was purified by flash chromatography eluting with 7% methanol in dichloromethane containing 0.7% of ammonium hydroxide to yield 0.179 g of 5-(imino-morpholin-4-yl-methyl)-3,4-dihydro-1H-isoquinoline 28a.

Step 4

2-[5-(Imino-morpholin-4-yl-methyl)-3,4-dihydro-1H-isoquinolin-2-yl]-6,7-dimethoxy-3H-quinazolin-4-one A mixture of 2-chloro-6,7-dimethoxy-3H-quinazolin-4-one 1b (0.159 g, 0.62 mmol) and 5-(imino-morpholin-4-yl-methyl)-3,4-dihydro-1H-isoquinoline 28a (0.179 g, 0.69 mmol) in methoxyethanol (10 mL) was heated to 95° C. with stirring for 18 h. the volatiles were evaporated and the residue was purified by flash column eluting with 2% methanol in dichloromethane containing 0.2% of ammonium hydroxide to yield 50 mg of 2-[5-(imino-morpholin-4-yl-methyl)-3,4-dihydro-1H-isoquinolin-2-yl]-6,7-dimethoxy-3H-quinazolin-4-one 901. The product was converted to the hydrochloric acid salt, mp. 249–251° C., [M+H]$^+$=450.

Example 10

2-[5-(4-Amino-pyridin-3-yl)-3,4-dihydro-1H-isoquinolin-2-yl]-6,7-dimethoxy-3H-quinazolin-4-one

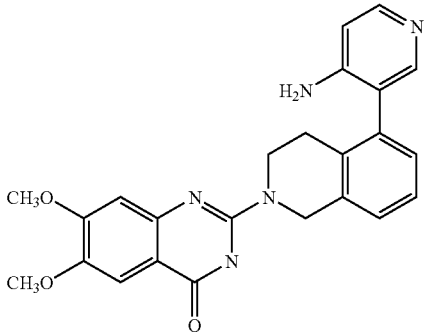

Step 1:

(3-Tributylstannanyl-pyridin-4-yl)-carbamic acid tert-butyl ester

Pyridin-4-yl-carbamic acid tert-butyl ester (1.74 g, 8.95 mmol) (prepared as described in Venuti et al, *J. Med. Chem.* 1988, 31(11), 2136–45) dissolved in THF (150 mL) was cooled to −78° C. and a solution of 1.7M tert-butyllithium in hexanes (11.6 mL, 19.70 mmol) was added dropwise. After the addition, the stirring was continued for 1 h to −78° C. and the solution was then allowed to warm to −20° C. and stirred for an additional 3 h. The reaction was cooled again to −78° C. and tributyltin chloride (2.91 mL, 10.74 mmol) was added dropwise and the reaction was allowed to reach room temperature overnight. A saturated ammonium chloride solution was added and the product extracted with dichloromethane. The combined organics were dried over magnesium sulfate, the solvent was evaporated and residue purified by flash chromatography eluting with 20% ethyl acetate in hexanes to yield 2.12 g of (3-tributylstannyl-pyridin-4-yl)-carbamic acid tert-butyl ester.

Step 2:

5-(4-tert-Butoxycarbonylamino-pyridin-3-yl)-3,4-dihydro-1H-isoquinoline-2-carboxylic acid tert-butyl ester A mixture of (3-tributylstannyl-pyridin-4-yl)-carbamic acid tert-butyl ester (0.7 g, 1.44 mmol), 5-bromo-3,4-dihydro-1H-isoquinoline-2-carboxylic acid tert-butyl ester (0.45 g, 1.44 mmol), tris(dibenzylideneacetone)dipalladium(0) (0.066 g, 0.072 mmol) and 2-(cyclohexylphosphino)biphenyl (0.075 g, 0.216 mmol), in toluene was heated with stirring to 100° C. for 24 h. The solvent was evaporated and the residue purified by flash chromatography eluting with 50% ethyl acetate in hexanes to yield 0.18 g 5-(4-tert-butoxycarbonylamino-pyridin-3-yl)-3,4-dihydro-1H-isoquinoline-2-carboxylic acid tert-butyl ester).

Step 3:

3-(1,2,3,4-Tetrahydro-isoquinolin-5-yl)-pyridin-4-ylamine 5-(4-tert-Butoxycarbonylamino-pyridin-3-yl)-3,4-dihydro-1H-isoquinoline-2-carboxylic acid tert-butyl ester (0.18 g, 0.42 mmol) was dissolved at room temperature in 20 mL of 10% trifluoroacetic acid in dichloromethane and stirred to room temperature for 18 h. The volatiles were evaporated, the residue was suspended in toluene and evaporated again. The residue was purified by flash chromatography eluting with 7% methanol in dichloromethane containing 0.7% of ammonium hydroxide to yield 0.075 g of 3-(1,2,3,4-tetrahydro-isoquinolin-5-yl)-pyridin-4-ylamine.

Step 4

2-[5-(4-Amino-pyridin-3-yl)-3,4-dihydro-1H-isoquinolin-2-yl]-6,7-dimethoxy-3H-quinazolin-4-one A mixture of 2-chloro-6,7-dimethoxy-3H-quinazolin-4-one 1b (0.076 g, 0.31 mmol) and 3-(1,2,3,4-tetrahydro-isoquinolin-5-yl)-pyridin-4-ylamine (0.075 g, 0.33 mmol) in methoxyethanol (5 mL) was heated to 95° C. with stirring for 18 h the volatiles were evaporated and the residue was purified by flash column eluting with 2% methanol in dichloromethane containing 0.2% of ammonium hydroxide to yield 2-[5-(4-amino-pyridin-3-yl)-3,4-dihydro-1H-isoquinolin-2-yl]-6,7-dimethoxy-3H-quinazolin-4-one 902. The product was converted to the hydrochloric acid salt, mp. >300° C., [M+H]$^+$=430.

Example 11

6,7-Dimethoxy-2-(5-morpholin-4-yl-3,4-dihydro-1H-[2,6]naphthyridin-2-yl)-3H-quinazolin-4-one

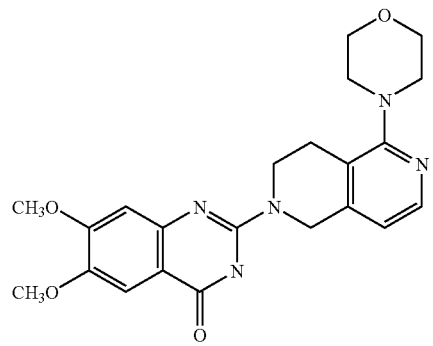

To 1-chloro-2,6-naphthyridine (164.3 mg, 0.998 mmol) (prepared as described in Van den Haak et al, *J. Org. Chem* 1982, 47 (9), 1673–7) was added morpholine (15 mL) and the mixture was heated at reflux for 4 h. Removal of the volatile components gave 216.6 mg of 1-morpholin-4-yl-[2,6]naphthyridine as a beige solid.

Reduction using 10% palladium on carbon in acetic acid at 50–60 psi or Adam's catalyst as described in Example 3 or 4, Step 1 yields 5-morpholin-4-yl-1,2,3,4-tetrahydro-[2,6]naphthyridine, which was further coupled as described herein with 2-chloro-6,7-dimethoxy-3H-quinazolin-4-one 1b and purified by HPLC to give 6,7-Dimethoxy-2-(5-morpholin-4-yl-3,4-dihydro-1H-[2,6]naphthyridin-2-yl)-3H-quinazolin-4-one, 903 [M+H]$^+$=424.

Example 12

6,7-Dimethoxy-2-(3-phenyl-5,6-dihydro-8H-imidazo[1,2-α]pyrazin-7-yl)-1H-quinazolin-4-one

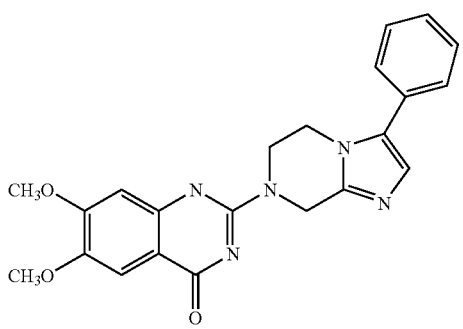

5,6,7,8-Tetrahydro-imidazo[1,2-a]pyrazine, prepared as described in PCT Application WO 01/44250, was coupled with 2-chloro-6,7-dimethoxy-3H-quinazolin-4-one 1b, as described herein. 2-(5,6-dihydro-8H-imidazo[1,2-a]pyrazin-7-yl)-6,7-dimethoxy-1H-quinazolin-4-one (150 mg, 0.46 mmol) was combined with bromobezene (97 μL, 0.92 mmol), potassium carbonate (127 mg, 0.92 mmol), palladium acetate (5 mg, 5 mol %), and triphenylphosphine (13 mg, 10 mol %) in DMF (6 mL). The mixture was heated in a 140° C. bath for 2 d, then concentrated onto silica gel followed by eluting with 300:10:1 $CH_2Cl_2$:MeOH:$NH_4OH$) to afford 50 mg of 6,7-dimethoxy-2-(3-phenyl-5,6-dihydro-8H-imidazo[1,2-α]pyrazin-7-yl)-1H-quinazolin-4-one, 904, mp: >300° C, $M^+$=403.

Coupling benzyl-(2-phenyl-5,6,7,8-tetrahydro-imidazo[1,2-a]pyrazin-3-yl)-amine (prepared by reduction of benzyl-(2-phenyl-imidazo[1,2-a]pyrazin-3-yl)-amine, as described in Balckburn et al., *Tetrahedron Lett.* 1998, 39(22), 3635–3638) with 2-chloro-6,7-dimethoxy-3H-quinazolin-4-one 1b, as described herein the following compound was prepared:

2-(3-benzylamino-2-phenyl-5,6-dihydro-8H-imidazo[1,2α]pyrazin-7-yl)-6,7-dimethoxy-1H-quinazolin-4-one, 905, mp=282–283, $M^+$=508.

Example 13

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 14

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 15

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Example 16

Parenteral Formulation (IV)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 17

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 18

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and additional water is then added q.s. about 100 g.

Example 19

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 20

[$^3$H]prazosin Binding (Alpha1-Adrenoceptor) Assay

Alpha-1A, alpha1B, and alpha1D adrenoceptortransfected CHO-K1 cells, prepared using the methods described by Chang et al., FEBS Lett. 1998, 422:279–283, were grown to confluence in T-162 tissue culture flasks in Ham's F-12 culture medium supplemented with 10% fetal bovine serum, geneticin (150 μg/mL) and streptomycin/penicillin (30 μg/mL/30 μg/mL) at 37° C. in 7% $CO_2$. Cells were harvested by incubating with phosphate-buffered saline (PBS) containing 30 μM EDTA for 5–10 min at 37° C. Cells were pelleted by centrifuging at 500×g for 5 min, and the pelleted cells were homogenized (Polytron homogenizer) in 10 vols (w/v) of 50 mM Tris, 1 mM EDTA, (homogenisation buffer, pH 7.4 at 4° C.). The homogenate was centrifuged at 45,000×g for 20 min. The pellet was resuspended in the homogenizing buffer and rehomogenized. The resulting homogenate was centrifuged at 45,000×g for 20 min. The pellet was resuspended in 50 mM Tris buffer (pH 7.4 at 4° C.), aliquoted, frozen, and stored at −80° C. for further use.

The membranes were thawed at room temperature and diluted in assay buffer (50 mM Tris buffer at pH 4) at 37° C. and homogenized using the Polytron tissue disrupter. The membranes were incubated with the radioligand ([$^3$H]prazosin, NEN, 0.1–0.5 nM) and test compound at 37° C. for 30 min. The membranes were then filtered over polyethyleneimine-treated GF/B unifilter plates using a Packard Filtermate Harvester and washed with ice-cold 50 mM Tris-HCl, 1 mM EDTA buffer (3×3 sec. washes). Scintillation cocktail was added to the filter plates and bound radioligand determined by liquid scintillation spectrophotometry.

For each experiment, total binding (in the absence of any test or reference compounds) and non-specific binding (10 μM phentolamine) were determined. For each sample tested, the concentration producing 50% inhibition of binding ($IC_{50}$) and Hill Slope ($n_H$) was determined using iterative non-linear curve fitting techniques with Kaleidagraph (Synergy Software) or other appropriate software. If the radioligand $K_D$ was known, the inhibition dissociation constant ($K_I$) of each ligand was determined according to the method of Cheng and Prusoff (Cheng, Y-C. and Prusoff, W. H., Biochem. Pharmacol., 1973, 22, 3099–3108).

Proceeding as in Example 20, compounds of Formula I were tested and found to be selective alpha-1A/B-adrenoceptor antagonists.

Example 21

Rat In Vivo, Blood Pressure Assay

The following describes an in vivo assay for measuring the effect of test compounds on blood pressure in normotensive and spontaneously hypertensive rats.

Normotensive or spontaneously hypertensive rats (0.25 to 0.45 kg) were fasted for 18 h and anesthetized with ether. The right femoral vein was isolated and cannulated with a fluid filled polyethylene cannula for bolus administration of test substances. The right femoral artery was isolated and cannulated with a fluid filled polyethylene cannula connected to an external pressure transducer for monitoring mean arterial blood pressure (MAP).

Following cannulation, rats were pretreated (intravenous route) with an angiotensin receptor antagonist, a beta-adrenergic receptor antagonist and an alpha-2 adrenergic receptor antagonist as described in Blue et al. Br. J. Pharmacol. 1997, 120, 107P.

The rats were placed in restrainers and allowed to recover from anesthesia. Following a 30–60 minute period for stabilization, the test compounds or vehicles were administered intravenously. Following the last dose of test compound, prazosin was optionally administered, i.v., to determine hypotensive effects obtained by non-subtype-selective blockade of alpha1-adrenoceptors. Blood pressure and heart rate are monitored continuously for at least 4 hrs. post-administration.

Proceeding as in Example 21 compounds of Formula I were tested and found to be considerably less potent than prazosin at producing blood pressure lowering effects.

Example 22

Pain Response to Radiant Heat in Neuropathic Rats

The following describes an in vivo assay for measuring the effect of test compounds on the pain response to radiant heat in neuropathic rats.

Male Sprague-Dawley rats (Harlan, 240–300 g) are surgically prepared to have a chronic constriction injury (CCI) as described above 13–15 days prior to testing. Rats are selected for the study according to the following criteria: ligated leg ($L_L$) latency—4 to 14 seconds; sham leg ($L_S$) latency—6 to 18 seconds; difference ($L_{Diff}=L_L-L_S$)—greater than 1.5 seconds. Selected rats are randomly assigned to treatment groups and dosed at 0 (vehicle, 10 mL/kg, 0.5% CMC, 30, 60, 100 or 300 µg/kg, ip. After 1 hour post-dosing, rats are placed under inverted plastic cages on an elevated glass platform. For each rat, four trials of each of the following are performed: shone light on the left hind paw (sham) and recorded the latency when the paw is withdrawn; shone light on the right hind paw (ligated) and recorded the latency when the paw is withdrawn. Five minute intervals are allowed between trials. Hind paws are examined for redness and blistering after each test.

Proceeding as in Example 22, compounds of Formula I are tested and assayed for a significant effect in the radiant heat assay.

Example 23

Cold Allodynia Response in Neuropathic Rats

The following describes an in vivo assay for measuring the effect of test compounds on the cold allodynia response in neuropathic rats.

Male Sprague-Dawley rats (Harlan, 160–200 g) were surgically prepared to have a chronic constriction injury (CCI) as described above 6 days prior to testing. Rats were selected for the study according to the following criteria: 1) the average of two trials was less than or equal to 13 sec; and 2) there was consistency across the two trial scores. Animals were screened for hypersensitivity to cold on post-surgery days 4 through 10, and selected for inclusion in dose-response studies based on the criteria described above. The pre-dose screening values were used as the animals' baseline cold allodynia scores.

Selected rats were tested twice in the cold bath assay described above for a pre-dose baseline and randomly assigned to treatment groups and dosed at 0 (vehicle, 10 mL/kg, 0.5% CMC, 30, 100 or 300 µg/kg, ip. After 1 hour and 3 hours post-dosing, rats were tested in the cold bath assay. For each rat, the assay was run once at 1 and 3 hours post-dose. The time to raise the rear leg was recorded in each trial. The maximal observing time in each trial was 20 seconds.

Proceeding as in Example 23, compounds of Formula I were tested and assayed for a significant effect in the cold allodynia response assay.

Example 24

Dog In Vivo Blood and Intraurethral Pressure Assay

The following describes an in vivo assay for measuring the relative effect of test compounds on hypogastric nerve stimulation-induced increases in intraurethral pressure and phenylephrine-induced increases in diastolic blood pressure in anesthetized dog.

Mongrel dogs (10 to 20 kg) were fasted for 12 to 18 hours and anesthetized with phenobarbital sodium (35 mg/kg, i.v.). An endotracheal tube was inserted and thereafter the lungs were mechanically ventilated with room air. The right femoral vein was isolated and cannulated with two polyethylene cannulae, one for the administration of a continuous infusion of phenobarbital sodium (5 to 10 mg/kg/hr) and the other for bolus administration of test substances. The right femoral artery was isolated and cannulated to the abdominal aorta with a fluid filled polyethylene cannula connected to an external pressure transducer for monitoring diastolic aortic pressure (DAP). The bladder was exposed via a ventral midline abdominal incision and emptied of urine through a 22 gauge needle. The bladder was cannulated through a stab incision with a water filled balloon catheter connected to an external pressure transducer for monitoring prostatic intraurethral pressure (IUP). The right hypogastric nerve (HGN) was carefully isolated and attached to a Dastre's electrode for nerve stimulation.

The preparation was allowed to stabilize for at least 30 minutes and must have had a stable basal IUP for not less than 15 minutes prior to commencement of the assay protocol. The HGN was stimulated (20–50V, 10 Hz, 10 msec pulse train for 10 sec) to induce a measurable increase in IUP and then phenylephrine (PE) was administered by bolus injection (0.5 to 0.6 µg/kg, i.v.) to induce a measurable increase in DAP. The HGN stimulation and PE bolus injection were repeated every 5 minutes until three consecutive reproducible increases in IUP and DAP were achieved. Vehicle (0.1 to 0.3 mL/kg) was administered and 20 minutes later the HGN stimulation and PE bolus injection were repeated. Test compound was then administered and 20 minutes later the HGN stimulation and PE bolus injection were repeated. Test compound was administered approximately every 20 minutes, increasing the dose until maximal or near maximal inhibition of the increases in IUP and DAP is attained.

Proceeding as in Example 24, compounds of Formula I were tested and found to selectively inhibit the HGN stimulation-induced increases in IUP. In contrast, prazosin inhibited increases in IUP and DAP in similar fashion.

Example 25

Blood Withdrawal Model in Conscious Rat

Short-term maintenance of blood pressure during postural changes, such as on standing (when venous return to the heart is compromised by blood pooling in the lower extremities) is critically dependent on sympathetic vasoconstriction, mediated via alpha1-adrenoceptors. Since clinical use of non-subtype selective alpha1-adrenoceptor antagonists is known to be associated with significant incidence of postural hypotension, this model, in which venous pooling has been mimicked by blood withdrawal, has been used to assess the potential of alpha1-adrenoceptor antagonists to cause this side effect.

Male Sprague-Dawley Rats (360–540 g) were anesthetized with metofane. An inguinal skin incision was made on the hind limb of the animal. Both the left and right femoral arteries and the left femoral vein were isolated and cannulated with PE-50 fluid-filled cannula for measurement of blood pressure, withdrawal of blood and administration of compound, respectively. The incision site was closed using 9 mm auto-clips. Animals were then placed in Bollman cages with their tails secured with masking tape.

Following recovery from anesthesia, a 1 hour stabilization period was allowed. Four mL of blood were then withdrawn into a heparinized syringe, and the effect on blood pressure and heart rate was noted. Five to seven minutes later the blood was returned to the rat. After another 1 hour stabilization period, test compound or vehicle was administered (i.v.). The blood withdrawal procedure was repeated 10 minutes after administration of vehicle or test compound. Blood pressure and heart rate were monitored continuously throughout the experiment using a Gould polygraph (Model MK200A) and Buxco data acquisition computer system.

Changes in blood pressure following blood withdrawal were compared before and after dosing with test compound.

Proceeding as in Example 25, compounds of Formula I were tested for postural hypotension.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound comprising Formula I:

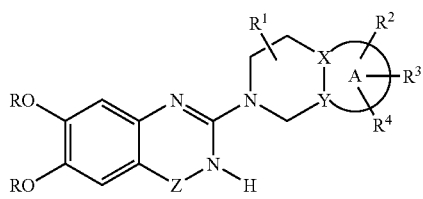

wherein:
X is carbon or nitrogen;
Y is carbon;
and X-Y considered together are two adjoining atoms of the ring A, said ring being a fused aromatic ring of five to six atoms per ring optionally incorporating one to two heteroatoms per ring, chosen from N, O, or S;
Z is —S(O)$_2$—;
R is lower alkyl;
R$^1$ is hydrogen; lower alkyl;
aryl; arylalkyl; arylaminocarbonyl; wherein the aryl group is optionally substituted with one to two substituents selected from lower alkyl, halo, cyano and lower alkoxy;
heteroaryl or heteroarylalkyl, wherein the aryl group is optionally substituted with one or two substituents selected from the group consisting of lower alkyl, halogen, cyano, and lower alkyl;

R$^2$, R$^3$, and R$^4$ are each independently in each occurrence selected from:
hydrogen; lower alkyl;
cycloalkyl or cycloalkylalkyl, wherein the cycloalkyl group is optionally substituted with one, two, or three substituents selected from the group consisting of hydroxy, cyano, lower alkyl, lower alkoxy, halo-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and phenyl optionally substituted with one or two substituents selected from the group consisting of lower alkyl, halogen, cyano and lower alkoxy;
aryl or arylalkyl, wherein the aryl group is optionally substituted with one, two, or three substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino, or two adjacent atoms of the aryl ring can be substituted with a methylenedioxy or ethylenedioxy group;
heterocyclyl or heterocyclylalkyl, wherein the heterocyclyl group is optionally substituted with one, two, or three substituents selected from the group consisting of hydroxy, hydroxyalkyl, oxo, cyano, cyanoalkyl, lower alkyl, lower alkoxy, alkoxyalkyl, halogen-lower alkoxy, alkylthio, halogen, haloalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino;
heteroaryl or heteroarylalkyl, wherein the heteroaryl group is optionally substituted with one, two, or three substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino;
hydroxy; hydroxyalkyl; alkoxy; alkoxyalkyl;
halo; haloalkyl; cyano; cyanoalkyl; and —(CH$_2$)$_{0-3}$NR'R"; —C(NH)—NR'R"; —N—C(NR')—R"; —N=CR'—NR'R"; —SO$_2$NR'R"; —NSO$_2$R'; —C(O)R'; —C(O)NR'R"; or —NC(O)R';
with the proviso that if A is a phenyl ring, at least one of R$^2$, R$^3$ or R$^4$ is not hydrogen; or
R$^2$ and R$^3$, if adjacent, taken together wit the carbons to which they are attached may form a 5- to 7-membered aromatic, saturated or unsaturated ring, optionally incorporating one or two ring heteroatoms chosen from N, S, or O, which can be optionally substituted with one or two substituents selected from lower alkyl, halo, haloalkyl, cyano, alkylthio, and lower alkoxy; and R' and R" are independently in each occurrence selected from:
  hydrogen; lower alkyl; substituted lower alkyl; hydroxyalkyl; alkoxyalkyl;
  cycloalkyl, wherein the cycloalkyl group is optionally substituted wit one, two, or three substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and phenyl;
  aryl or arylalkyl, wherein the aryl group is optionally substituted with one, two, or three substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino, or two adjacent atoms of the aryl ring can be substituted with a methylenedioxy or ethylenedioxy group;
  heteroaryl or heteroarylalkyl, wherein the heteroaryl group is optionally substituted with one, two, or three substituents selected from the group consisting of hydroxy, cyano, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino;
  heterocyclyl or heterocyclylalkyl, wherein the heterocyclyl group is optionally substituted with one, two, or three substituents selected from the group consisting of hydroxy, oxo, cyano, cyanoalkyl, lower alkyl, lower alkoxy, halogen-lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, and arylcarbonylamino;
  or R' and R" together with the nitrogen to which they are attached may form a 5- to 7-membered ring, optionally incorporating one additional ring heteroatom chosen from N, O or S; wherein this ring is optionally substituted wit one or two substituents selected from the group consisting of lower alkyl, halogen, cyano, lower alkoxy and phenyl optionally substituted with one or two substituents selected from the group consisting of lower alkyl, halogen, cyano and lower alkoxy;
  or pharmaceutically acceptable salts thereof.

2. The compound of claim 1, wherein X is carbon.
3. The compound of claim 1, wherein X is nitrogen.
4. The compound of claim 1, wherein $R^1$ is hydrogen.
5. The compound of claim 4, wherein X is carbon and A is a fused aryl ring.
6. The compound of claim 5, wherein A is a fused phenyl ring.
7. The compound of claim 4, wherein X is carbon and A is a fused heteroaryl ring.
8. The compound of claim 7, wherein A is a fused pyrimidine ring.
9. The compound of claim 7, wherein A is a fused pyrrole ring.
10. The compound of claim 9, wherein $R^2$ and $R^3$ taken together with the carbons to which they are attached form a fused phenyl ring, optionally substituted with one or two substituents selected from lower alkyl, halo, haloalkyl, cyano, alkylthio, and lower alkoxy.
11. The compound of claim 7, wherein A is a fused pyridine ring.
12. The compound of claim 7, wherein A is a fused imidazole ring.
13. The compound of claim 4, wherein X is nitrogen and A is a fused imidazole ring.
14. The compound of claim 4, wherein $R^2$ is —$(CH_2)_{0-3}$NR'R" or —$SO_2$NR'R", and wherein R' and R" are independently in each occurrence hydrogen, lower alkyl, substituted lower alkyl, cycloalkyl, aryl, arylalkyl, heteroaryl, and heteroarylalkyl, or R' and R" together with the nitrogen to which they are attached may form a 5- to 7-membered ring, optionally incorporating one additional ring heteroatom chosen from N, O, or S.
15. The compound of claim 6, wherein $R^2$ is —$(CH_2)_{0-3}$NR'R" or —$SO_2$NR'R", and wherein R' and R" are independently in each occurrence selected from hydrogen, lower alkyl, substituted lower alkyl, cycloalkyl, aryl, arylalkyl, heteroaryl, and heteroarylalkyl, or R' and R" together with the nitrogen to which they are attached may form a 5- to 7-membered ring, optionally incorporating one additional ring heteroatom chosen from N, O, or S.
16. The compound of claim 6, wherein $R^2$ is selected from the groups —C(NH)—NR'R", —N—C(NR')—R", and —N=CR'—NR'R", and wherein R' and R" are independently in each occurrence selected from hydrogen, lower alkyl, substituted lower alkyl, cycloalkyl, aryl, arylalkyl, heteroaryl, and heteroarylalkyl, or R' and R" together with the nitrogen to which they are attached may Coon a 5- to 7-membered ring, optionally incorporating one additional ring heteroatom chosen from N, O, or S.
17. A compound of claim 6, wherein $R^2$ is aryl or heteroaryl.
18. A compound of claim 6, wherein $R^2$ is alkoxy, cyano, or cyanoalkyl.
19. The compound of claim 8, wherein $R^2$ is —$(CH_2)_{0-3}$NR'R" or —$SO_2$NR'R", and wherein R' and R" are independently in each occurrence selected from hydrogen, lower alkyl, substituted lower alkyl, cycloalkyl, aryl, arylalkyl, heteroaryl, and heteroarylalkyl, or R' and R" together with the nitrogen to which they are attached may form a 5- to 7-membered ring, optionally incorporating one additional ring heteroatom chosen from N, O, or S.
20. The compound of claim 19, wherein $R^2$ is —NR'R", and wherein R' and R" taken with the nitrogen to which they are attached may form a 5- to 7-membered ring, optionally incorporating one additional ring heteroatom chosen from N, O, or S.
21. The compound of claim 13, wherein $R^2$ is —$(CH_2)_{0-3}$NR'R" or —$SO_2$NR'R", and wherein R' and R" are independently in each occurrence selected from hydrogen, lower alkyl, substituted lower alkyl, cycloalkyl, aryl, arylalkyl, heteroaryl, and heteroarylalkyl, or R' and R' together with the nitrogen to which they are attached may form a 5-to 7-membered ring, optionally incorporating one additional ring heteroatom chosen from N, O or S.

22. The compound of claim 1, wherein the compound is:

3-(6,7-dimethoxy-3,4-dihydro-1H-isoquinolin-2-yl)-6,7-dimethoxy-2H-benzo[1,2,4]-thiadiazine-1,1-dioxide;

2-(cyclohexylamino-5,6-dihydro-8H-imidazo[1,5-a]pyrazin-7-yl)-6,7-dimethoxy-2H-benzo[1,2,4]thiadiazine-1,1-dioxide;

6,7-dimethoxy-3-(4-morpholin-4-yl-5,8-dihydro-6H-pyrido[3,4-d]pyrimidin-7-yl)-2H-benzo[1,2,4]thiadiazine-1,1-dioxide;

or a pharmaceutically-acceptable salt thereof.

23. A pharmaceutical composition comprising a therapeutically effective amount of a compound of claim 1 in admixture with a pharmaceutically acceptable carrier.

24. A process for preparing a compound as claimed in claim 1, which process comprises reacting a compound of Formula II

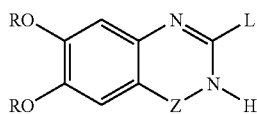

wherein L is a leaving group, and R and Z are as defined in claim 1, with a compound of Formula III:

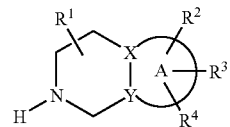

wherein $R^1$, $R^2$, $R^3$, $R^4$, X, and Y are as defined in claim 1, optionally in the presence of a base to provide a compound of Formula I:

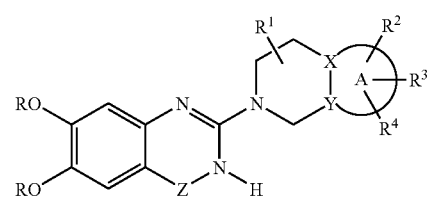

wherein R, $R^1$, $R^2$, $R^3$, $R^4$, X, Y, Z, and A are as defined in claim 1.

* * * * *